US006368601B1

(12) United States Patent
Allan et al.

(10) Patent No.: US 6,368,601 B1
(45) Date of Patent: Apr. 9, 2002

(54) PORCINE CIRCOVIRUS VACCINE AND DIAGNOSTICS REAGENTS

(75) Inventors: Gordon Allan; Brian Meehan, both of Belfast (GB); Edward Clark, Saskatoon (CA); John Ellis, Saskatoon (CA); Deborah Haines, Saskatoon (CA); Lori Hassard, Saskatoon (CA); John Harding, Humboldt (CA); Catherine Elisabeth Charreyre, Saint-Laurent de Mure (FR); Gilles Emile Chappuis, Lyons (FR); Francis McNeilly, Newtownards (GB)

(73) Assignees: Merial, Lyons (FR); The Queen's University of Belfast, Belfast (GB); University of Saskatchewan, Saskatoon (CA)

( * ) Notice: Subject to any disclaimer, the term of this patent is extended or adjusted under 35 U.S.C. 154(b) by 0 days.

(21) Appl. No.: 09/082,558

(22) Filed: May 21, 1998

(30) Foreign Application Priority Data

| | | |
|---|---|---|
| Oct. 3, 1997 | (FR) | 97 12382 |
| Jan. 22, 1998 | (FR) | 98 00873 |
| Mar. 20, 1998 | (FR) | 98 03707 |

(51) Int. Cl.[7] .......................... A61K 39/12; A61K 31/70; C12Q 1/70; C12H 15/00; C12N 7/00

(52) U.S. Cl. .......................... 424/204.1; 514/44; 435/5; 435/235.1; 435/320.1; 536/23.1; 536/23.4

(58) Field of Search .............................. 536/23.1, 23.4; 435/5, 320.1, 235.1; 514/44; 424/204.1

(56) References Cited

U.S. PATENT DOCUMENTS 6,217,883 B1 * 4/2001 Allan et al. .............. 424/201.1

FOREIGN PATENT DOCUMENTS

| | | |
|---|---|---|
| FR | 2772047 | * 6/1999 |
| WO | 99/29717 | * 6/1999 |

OTHER PUBLICATIONS

Tischer et al. 1982. A very small porcine virus with circular single–stranded DNA. Nature. vol. 295, pp. 64–66.*

Sequence Alignments, for SEQ ID NO:s 1–4 and 6 with Genbank Acc No: 027217, Sep. 27, 1997 (Hamel et al.).*

Nayar et al., Canadian Veterinary Journal, vol. 38, Jun. 1997, pp. 385–386.

E.G. Clark, American Association of Swine Practioners, 1997, pp. 499–501.

Meehan et al., Journal of General Virology, vol. 78, 1997, pp. 221–227.

Todd et al., Arch. Virol., vol. 117, 1991, pp. 129–135.

LeCann et al., Veterinary Record, Dec. 20/27, 1997, p. 660.

Daft et al., 39$^{th}$ Annual Meeting of American Association of Veterinary Laboratory Diagnosticians, Oct. 12–18, 1996.

Harding et al., American Association of Swine Practioners, 1997, p. 503.

Albina et al., La Semaine Veterinaire des Filieres, No. 26, Nov. 30, 1996, pp. 1–2.

V. Dedet, La Semaine Veterinaire, May 24, 1997, p. 54.

Allan et al., J. Vet. Diagn. Invest., vol. 10 (1998), pp. 3–10.

Ellis et al., Can. Vet. J., vol. 39, Jan. 1998, pp. 44–51.

Segales et al., Veterinary Record, Dec. 6, 1997, pp. 600–601.

Allan et al., Vet. Immunol. Immunopathol., vol. 43 (1994), pp. 357–371.

Allan et al., Vet. Micro., vol. 44 (1995), pp. 49–64.

Tischer et al., Arch. Virol., vol. 91 (1986), pp. 271–276.

Hamel et al., Database EMBL/Genbank/DDBJ, Sep. 26, 1997.

* cited by examiner

*Primary Examiner*—Laurie Scheiner
*Assistant Examiner*—Shanon A. Foley
(74) *Attorney, Agent, or Firm*—Frommer Lawrence & Haug, LLP; William S. Frommer; Thomas J. Kowalski

(57) ABSTRACT

The invention relates to new porcine circovirus strains isolated from pulmonary or ganglionic samples obtained from farms affected by the post-weaning multisystemic wasting syndrome (PMWS). It relates to purified preparations of these strains, conventional attenuated or inactivated vaccines, recombinant live vaccines, plasmid vaccines and subunit vaccines, as well as reagents and diagnostic methods. It also relates to the DNA fragments which can be used for the production of subunits in an in vitro expression vector or as sequences to be integrated into a virus or plasmid type in vivo expression vector.

35 Claims, 18 Drawing Sheets

Figure No. 1

Sequence of the PCV Imp1011-48121 isolate (SEQ ID No. 1)

```
   1 AATTCAACCT TAACCTTTCT TATTCTGTAG TATTCAAAGG GCACAGAGCG
  51 GGGGTTTGAG CCCCCTCCTG GGGGAAGAAA GTCATTAATA TTGAATCTCA
 101 TCATGTCCAC CGCCCAGGAG GGCGTTCTGA CTGTGGTTCG CTTGACAGTA
 151 TATCCGAAGG TGCGGGAGAG GCGGGTGTTG AAGATGCCAT TTTTCCTTCT
 201 CCAGCGGTAA CGGTGGCGGG GGTGGACGAG CCAGGGGCGG CGGCGGAGGA
 251 TCTGGCCAAG ATGGCTGCGG GGGCGGTGTC TTCTTCTCCG GTAACGCCTC
 301 CTTGGATACG TCATATCTGA AAACGAAAGA AGTGCGCTGT AAGTATTACC
 351 AGCGCACTTC GGCAGCGGCA GCACCTCGGC AGCACCTCAG CAGCAACATG
 401 CCGAGCAAGA AGAATGGAAG AAGCGGACCC CAACCCCATA AAAGGTGGGT
 451 GTTCACTCTG AATAATCCTT CCGAAGACGA GCGCAAGAAA ATACGGGATC
 501 TTCCAATATC CCTATTTGAT TATTTTATTG TTGGCGAGGA GGGTAATGAG
 551 GAAGGACGAA CACCTCACCT CCAGGGGTTC GCTAATTTTG TGAAGAAGCA
 601 GACTTTTAAT AAAGTGAAGT GGTATTTGGG TGCCCGCTGC CACATCGAGA
 651 AAGCGAAAGG AACAGATCAG CAGAATAAAG AATACTGCAG TAAAGAAGGC
 701 AACTTACTGA TGGAGTGTGG AGCTCCTAGA TCTCAGGGAC AACGGAGTGA
 751 CCTGTCTACT GCTGTGAGTA CCTTGTTGGA GAGCGGGAGT CTGGTGACCG
 801 TTGCAGAGCA GCACCCTGTA ACGTTTGTCA GAAATTTCCG CGGGCTGGCT
 851 GAACTTTTGA AAGTGAGCGG GAAAATGCAG AAGCGTGATT GGAAGACTAA
 901 TGTAcACGTC ATTGTGGGGC CACCTGGGTG TGGTAAAAGC AAATGGGCTG
 951 CTAATTTTGC AGACCCGGAA ACCACATACT GGAAACCACC TAGAAACAAG
1001 TGGTGGGATG GTTACCATGG TGAAGAAGTG GTTGTTATTG ATGACTTTTA
1051 TGGCTGCCTG CCCTGGGATG ATCTACTGAG ACTGTGTGAT CGATATCCAT
1101 TGACTGTAGA GACTAAAGGT GGAACTGTAC CTTTTTTGGC CCGCAGTATT
1151 CTGATTACCA GCAATCAGAC CCCGTTGGAA TGGTACTCCT CAACTGCTGT
1201 CCCAGCTGTA GAAGCTCTTT ATCGGAGGAT TACTTCCTTG GTATTTTGGA
```

Figure No. 1 (continuation and end)

```
1251  AGAATGCTAC AGAACAATCC ACGGAGGAAG GGGGCCAGTT CGTCACCCTT
1301  TCCCCCCCAT GCCCTGAATT TCCATATGAA ATAAATTACT GAGTCTTTTT
1351  TATCACTTCG TAATGGTTTT TATTATTCAT TAAGGGTTAA GTGGGGGGTC
1401  TTTAAGATTA AATTCTCTGA ATTGTACATA CATGGTTACA CGGATATTGT
1451  ATTCCTGGTC GTATATACTG TTTTCGAACG CAGTGCCGAG GCCTACGTGG
1501  TCtACATTTC CAGCAGTTTG TAGTCTCAGC CACAGCTGGT TTCTTTTGTT
1551  GTTTGGTTGG AAGTAATCAA TAGTGGAATC TAGGACAGGT TTGGGGGTAA
1601  AGTAGCGGGA GTGGTAGGAG AAGGGCTGGG TTATGGTATG GCGGGAGGAG
1651  TAGTTTACAT AGGGGTCATA GGTGAGGGCT GTGGCCTTTG TTACAAAGTT
1701  ATCATCTAGA ATAACAGCAC TGGAGCCCAC TCCCTGTCA CCCTGGGTGA
1751  TCGGGAGCA GGGCCAG
```

Figure No. 2

Sequence of the PCV Imp1011-48285 isolate (SEQ ID No. 2)

```
   1 AATTCAACCT TAACCTTTCT TATTCTGTAG TATTCAAAGG GCACAGAGCG
  51 GGGGTTTGAG CCCCCTCCTG GGGGAAGAAA GTCATTAATA TTGAATCTCA
 101 TCATGTCCAC CGCCCAGGAG GGCGTTTTGA CTGTGGTTCG CTTGACAGTA
 151 TATCCGAAGG TGCGGGAGAG GCGGGTGTTG AAGATGCCAT TTTTCCTTCT
 201 CCAGCGGTAA CGGTGGCGGG GGTGGACGAG CCAGGGGCGG CGGCGGAGGA
 251 TCTGGCCAAG ATGGCTGCGG GGCGGTGTC TTCTTCTCCG GTAACGCCTC
 301 CTTGGATACG TCATATCTGA AAACGAAAGA AGTGCGCTGT AAGTATTACC
 351 AGCGCACTTC GGCAGCGGCA GCACCTCGGC AGCACCTCAG CAGCAACATG
 401 CCCAGCAAGA AGAATGGAAG AAGCGGACCC CAACCCCATA AAAGGTGGGT
 451 GTTCACTCTG AATAATCCTT CCGAAGACGA GCGCAAGAAA ATACGGGATC
 501 TTCCAATATC CCTATTTGAT TATTTTATTG TTGGCGAGGA GGGTAATGAG
 551 GAAGGACGAA CACCTCACCT CCAGGGGTTC GCTAATTTTG TGAAGAAGCA
 601 GACTTTTAAT AAAGTGAAGT GGTATTTGGG TGCCCGCTGC CACATCGAGA
 651 AAGCGAAAGG AACAGATCAG CAGAATAAAG AATACTGCAG TAAAGAAGGC
 701 AACTTACTGA TGGAGTGTGG AGCTCCTAgA TCTCAgGGAC AACGGAGTGA
 751 CCTGTCTACT GCTGTGAGTA CCTTGTTGGA GAGCGGGAGT CTGGTGACCG
 801 TTGCAGAGCA GCACCCTGTA ACGTTTGTCA GAAATTTCCG CGGGCTGGCT
 851 GAACTTTTGA AAGTGAGCGG GAAAATGCAG AAGCGTGATT GGAAGACTAA
 901 TGTACACGTC ATTGTGGGGC CACCTGGGTG TGGTAAAAGC AAATGGGCTG
 951 CTAATTTTGC AGACCCGGAA ACCACATACT GGAAACCACC TAGAAACAAG
1001 TGGTGGGATG GTTACCATGG TGAAGAAGTG GTTGTTATTG ATGACTTTTA
1051 TGGCTGGCTG CCCTGGGATG ATCTACTGAG ACTGTGTGAT CGATATCCAT
1101 TGACTGTAGA GACTAAAGGT GGAACTGTAC CTTTTTTGGC CCGCAGTATT
1151 CTGATTACCA GCAATCAGAC CCCGTTGGAA TGGTACTCCT CAACTGCTGT
1201 CCCAGCTGTA GAAGCTCTTT ATCGGAGGAT TACTTCCTTG GTATTTTGGA
```

Figure No. 2 (continuation and end)

```
1251  AGAATGCTAC AGAACAATCC ACGGAGGAAG GGGGCCAGTT CGTCACCCTT
1301  TCCCCCCCAT GCCCTGAATT TCCATATGAA ATAAATTACT GAGTCTTTTT
1351  TATCACTTCG TAATGGTTTT TATTATTCAT TAAGGGTTAA GTGGGGGGTC
1401  TTTAAGATTA AATTCTCTGA ATTGTACATA CATGGTTACA CGGATATTGT
1451  ATTCCTGGTC GTATATACTG TTTTCGAACG CAGTGCCGAG GCCTACGTGG
1501  TCTACATTTC CAGTAGTTTG TAGTCTCAGC CACAGCTGAT TTCTTTTGTT
1551  GTTTGGTTGG AAGTAATCAA TAGTGGAATC TAGGACAGGT TTGGGGGTAA
1601  AGTAGCGGGA GTGGTAGGAG AAGGGCTGGG TTATGGTATG GCGGGAgGAG
1651  TAGTTTACAT AGGGGTCATA GGTGAgGGCT GTGGCCTTTG TTACAAAGTT
1701  ATCATCTAGA ATAACAGCAC TGGAGCCCAC TCCCCTGTCA CCCTGGGTGA
1751  TCGGGGAGCA GGGCCAG
```

Figure No. 3

Sequence of the PCV Imp999 isolate (SEQ ID No. 3)

```
   1  AATTCAACCT TAACCTTTTT TATTCTGTAG TATTCAAAGG GTATAGAGAT
  51  TTTGTTGGTC CCCCCTCCCG GGGGAACAAA GTCGTCAATA TTAAATCTCA
 101  TCATGTCCAC CGCCCAGGAG GGCGTTCTGA CTGTGGTAGC CTTGACAGTA
 151  TATCCGAAGG TGCGGGAGAG GCGGGTGTTG AAGATGCCAT TTTTCCTTCT
 201  CCAACGGTAG CGGTGGCGGG GGTGGACGAG CCAGGGGCGG CGGCGGAGGA
 251  TCTGGCCAAG ATGGCTGCGG GGGCGGTGTC TTCTTCTGCG GTAACGCCTC
 301  CTTGGATACG TCATAGCTGA AAACGAAAGA AGTGCGCTGT AAGTATTACC
 351  AGCGCACTTC GGCAGCGGCA GCACCTCGGC AGCACCTCAG CAGCAACATG
 401  CCCAGCAAGA AGAATGGAAG AAGCGGACCC CAACCACATA AAAGGTGGGT
 451  GTTCACGCTG AATAATCCTT CCGAAGACGA GCGCAAGAAA ATACGGGAGC
 501  TCCCAATCTC CCTATTTGAT TATTTTATTG TTGGCGAGGA GGGTAATGAG
 551  GAAGGACGAA CACCTCACCT CCAGGGGTTC GCTAATTTTG TGAAGAAGCA
 601  AACTTTTAAT AAAGTGAAGT GGTATTTGGG TGCCCGCTGC CACATCGAGA
 651  AAGCCAAAGG AACTGATCAG CAGAATAAAG AATATTGCAG TAAAGAAGGC
 701  AACTTACTTA TTGAATGTGG AGCTCCTCGA TCTCAAGGAC AACGGAGTGA
 751  CCTGTCTACT GCTGTGAGTA CCTTGTTGGA GAGCGGGAGT CTGGTGACCG
 801  TTGCAGAGCA GCACCCTGTA ACGTTTGTCA GAAATTTCCG CGGGCTGGCT
 851  GAACTTTTGA AAGTGAGCGG GAAAATGCAG AAGCGTGATT GGAAGACCAA
 901  TGTACACGTC ATTGTGGGGC CACCTGGGTG TGGTAAAAGC AAATGGGCTG
 951  CTAATTTTGC AGACCCGGAA ACCACATACT GGAAACCACC TAGAAACAAG
1001  TGGTGGGATG GTTACCATGG TGAAgAAGTG GTTGTTATTG ATGACTTTTA
1051  TGGCTGGCTG CCGTGGGATG ATCTACTGAG ACTGTGTGAT CGATATCCAT
1101  TGACTGTAGA GACTAAAGGT GGAACTGTAC CTTTTTTGGC CCGCAGTATT
1151  CTGATTACCA GCAATCAGAC CCCGTTGGAA TGGTACTCCT CAACTGCTGT
1201  CCCAGCTGTA GAAGCTCTCT ATCGGAGGAT TACTTCCTTG GTATTTTGGA
```

Figure No. 3 (continuation and end)

```
1251  AGAATGCTAC AGAACAATCC ACGGAGGAAG GGGGCCAGTT CGTCACCCTT
1301  TCCCCCCCAT GCCCTGAATT TCCATATGAA ATAAATTACT GAGTCTTTTT
1351  TATCACTTCG TAATGGTTTT TATTATTCAT TTAGGGTTTA AGTGGGGGGT
1401  CTTTAAGATT AAATTCTCTG AATTGTACAT ACATGGTTAC ACGGATATTG
1451  TAGTCCTGGT CGTATATACT GTTTTCGAAC GCAGTGCCGA GGCCTACGTG
1501  GTCCACATTT CTAGAGGTTT GTAGCCTCAG CCAAAGCTGA TTCCTTTTGT
1551  TATTTGGTTG GAAGTAATCA ATAGTGGAGT CAAGAACAGG TTTGGGTGTG
1601  AAGTAACGGG AGTGGTAGGA GAAGGGTTGG GGGATTGTAT GGCGGGAGGA
1651  GTAGTTTACA TATGGGTCAT AGGTTAGGGC TGTGGCCTTT GTTACAAAGT
1701  TATCATCTAG AATAACAGCA GTGGAGCCCA CTCCCCTATC ACCCTGGGTG
1751  ATGGGGAGC AGGGCCAG
```

Figure No. 4

Sequence of the PCV Imp1010 isolate (SEQ ID No. 4)

```
   1  AATTCAACCT TAACCTTTCT TATTCTGTAG TATTCAAAGG GTATAGAGAT
  51  TTTGTTGGTC CCCCCTCCCG GGGGAACAAA GTCGTCAATT TTAAATCTCA
 101  TCATGTCCAC CGCCCAGGAG GGCGTTGTGA CTGTGGTACG CTTGACAGTA
 151  TATCCGAAGG TGCGGGAGAG GCGGGTGTTG AAGATGCCAT TTTTCCTTCT
 201  CCAACGGTAG CGGTGGCGGG GGTGGACGAG CCAGGGGCGG CGGCGGAGGA
 251  TCTGGCCAAG ATGGCTGCGG GGGCGGTGTC TTCTTCTGCG GTAACGCCTC
 301  CTTGGATACG TCATAGCTGA AAACGAAAGA AGTGCGCTGT AAGTATTACC
 351  AGCGCACTTC GGCAGCGGCA GCACCTCGGC AGCACCTCAG CAGCAACATG
 401  CCCAGCAAGA AGAATGGAAG AAGCGGACCC CAACCACATA AAAGGTGGGT
 451  GTTCACGCTG AATAATCCTT CCGAAGACGA GCGCAAGAAA ATACGGGAGC
 501  TCCCAATCTC CCTATTTGAT TATTTTATTG TTGGCGAGGA GGGTAATGAG
 551  GAAGGACGAA CACCTCACCT CCAGGGGTTC GCTAATTTTG TGAAGAAGCA
 601  AACTTTTAAT AAAGTGAAGT GGTATTTGGG TGCCCGCTGC CACATCGAGA
 651  AAGCCAAAGG AACTGATCAG CAGAATAAAG AATATTGCAG TAAAGAAGGC
 701  AACTTACTTA TTGAATGTGG AGCTCCTCGA TCTCAAGGAC AACGGAGTGA
 751  CCTGTCTACT GCTGTGAGTA CCTTGTTGGA GAGCGGGAGT CTGGTGACCG
 801  TTGCAGAGCA GCACCCTGTA ACGTTTGTCA GAAATTTCCG CGGGCTGGCT
 851  GAACTTTTGA AAGTGAGCGG GAAAATGCAG AAGCGTGATT GGAAGACCAA
 901  TGTACACGTC ATTGTGGGGC CACCTGGGTG TGGTAAAAGC AAATGGGCTG
 951  CTAATTTTGC AGACCCGGAA ACCACATACT GGAAACCACC TAGAAACAAG
1001  TGGTGGGATG GTTACCATGG TGAAGAAGTG GTTGTTATTG ATGACTTTTA
1051  TGGCTGGCTG CCGTGGGATG ATCTACTGAG ACTGTGTGAT CGATATCCAT
1101  TGACTGTAGA GACTAAAGGT GGAACTGTAC CTTTTTTGGC CCGCAGTATT
1151  CTGATTACCA GCAATCAGAC CCCGTTGGAA TGGTACTCCT CAACTGCTGT
1201  CCCAGCTGTA GAAGCTCTCT ATCGGAGGAT TACTTCCTTG GTATTTTGGA
```

Figure No. 4 (continuation and end)

```
1251  AGAATGCTAC AGAACAATCC ACGGAGGAAG GGGGCCAGTT CGTCACCCTT
1301  TCCCCCCCAT GCCCTGAATT TCCATATGAA ATAAATTACT GAGTCTTTTT
1351  TATCACTTCG TAATGGTTTT TATTATTCAT TTAGGGTTTA AGTGGGGGGT
1401  CTTTAAGATT AAATTCTCTG AATTGTACAT ACATGGTTAC ACGGATATTG
1451  TAGTCCTGGT CGTATTTACT GTTTTCGAAC GCAGCGCCGA GGCCTACGTG
1501  GTCCACATTT CCAGAGGTTT GTAGTCTCAG CCAAAGCTGA TTCCTTTTGT
1551  TATTTGGTTG GAAGTAATCA ATAGTGGAGT CAAGAACAGG TTTGGGTGTG
1601  AAGTAACGGG AGTGGTAGGA GAAGGGTTGG GGGATTGTAT GGCGGGAGGA
1651  GTAGTTTACA TATGGGTCAT AGGTTAGGGC TGTGGCCTTT GTTACAAAGT
1701  TATCATCTAG AATAACAGCA GTGGAGCCCA CTCCCTATC ACCCTGGGTG
1751  ATGGGGAGC AGGGCCAG
```

Figure No. 5

CLUSTAL W multiple sequence alignment

```
PCVPK-15    AATTCATATTTAGCCTTTCTAATACGGTAGTATTGGAAAGGTAGGGGTAGGGGGTTGGTG
IMP999-ECO  AATTCAACCTTAACCTTTTTTATTCTGTAGTATTCAAAGGGTATAGAGATTTTGTTGGTC
IMP1010-ST  AATTCAACCTTAACCTTTCTTATTCTGTAGTATTCAAAGGGTATAGAGATTTTGTTGGTC
IMP1011-48  AATTCAACCTTAACCTTTCTTATTCTGTAGTATTCAAAGGGCACAGAGCGGGGGTTTGAG
IMP1011-48  AATTCAACCTTAACCTTTCTTATTCTGTAGTATTCAAAGGGCACAGAGCGGGGGTTTGAG
            *****  *** ***** * ** * ********  ** **  *     ***  *

PCVPK-15    CCGCCTGAGGGGGGGAGGAACTGGCCGATGTTGAATTTGAGGTAGTTAACATTCCAAGAT
IMP999-ECO  CCCCCTCCCGGGGGAACAAAGTCGTCAATATTAAATCTCATCATGTCCACCGCCCAGGAG
IMP1010-ST  CCCCCTCCCGGGGGAACAAAGTCGTCAATTTTAAATCTCATCATGTCCACCGCCCAGGAG
IMP1011-48  CCCCCTCCTGGGGGAAGAAAGTCATTAATATTGAATCTCATCATGTCCACCGCCCAGGAG
IMP1011-48  CCCCCTCCTGGGGGAAGAAAGTCATTAATATTGAATCTCATCATGTCCACCGCCCAGGAG
            ** ***  ***** * ** *     ** ** *** * *       **  **   *** **

PCVPK-15    GGC--TGCGAGTATCCTCCTTTT-ATGGTGAGTACAAATTCTGTAGAAAGGCGGGAATTG
IMP999-ECO  GGCGTTCTGACTGTGGTAGCCTTGACAGTATATCCGAAGGTGCGGGAGAGGCGGGTGTTG
IMP1010-ST  GGCGTTGTGACTGTGGTACGCTTGACAGTATATCCGAAGGTGCGGGAGAGGCGGGTGTTG
IMP1011-48  GGCGTTCTGACTGTGGTTCGCTTGACAGTATATCCGAAGGTGCGGGAGAGGCGGGTGTTG
IMP1011-48  GGCGTTTTGACTGTGGTTCGCTTGACAGTATATCCGAAGGTGCGGGAGAGGCGGGTGTTG
            ***  *  **  *  *    *        ** * **         ** *******  ***

PCVPK-15    AAGATACCCGTCTTTCGGCGCCATCTGTAACGGTTTCTGAAGGCGGGGTGTGCCAAATAT
IMP999-ECO  AAGATGCCATTTTTCCTTCTCCAACGGTAGCGGTGGC-GGGGGTGGA-CGAGCCAGGGGC
IMP1010-ST  AAGATGCCATTTTTCCTTCTCCAACGGTAGCGGTGGC-GGGGGTGGA-CGAGCCAGGGGC
IMP1011-48  AAGATGCCATTTTTCCTTCTCCAGCGGTAACGGTGGC-GGGGGTGGA-CGAGCCAGGGGC
IMP1011-48  AAGATGCCATTTTTCCTTCTCCAGCGGTAACGGTGGC-GGGGGTGGA-CGAGCCAGGGGC
            *****  **   * **  *  * *** * *** ****     *  *    *    *****

PCVPK-15    GGTCTTCTCCGGAGGATGTTTCCAAGATGGCTGCGGGGGCGGGTCCTTCTTCTGCGGTAA
IMP999-ECO  GG----CGGCGGAGGATCTGGCCAAGATGGCTGCGGGGGCGGTGTCTTCTTCTGCGGTAA
IMP1010-ST  GG----CGGCGGAGGATCTGGCCAAGATGGCTGCGGGGGCGGTGTCTTCTTCTGCGGTAA
IMP1011-48  GG----CGGCGGAGGATCTGGCCAAGATGGCTGCGGGGGCGGTGTCTTCTTCTCCGGTAA
IMP1011-48  GG----CGGCGGAGGATCTGGCCAAGATGGCTGCGGGGGCGGTGTCTTCTTCTCCGGTAA
            **    *  ******** *  ******************** ********  ******

PCVPK-15    CGCCTCCTTGGCCACGTCATCCTATAAAAGTGAAAGAAGTGCGCTGCTGTAGTATTACCA
IMP999-ECO  CGCCTCCTTGGATACGTCATAGC-TGAAAACGAAAGAAGTGCGCTGTA--AGTATTACCA
IMP1010-ST  CGCCTCCTTGGATACGTCATAGC-TGAAAACGAAAGAAGTGCGCTGTA--AGTATTACCA
IMP1011-48  CGCCTCCTTGGATACGTCATATC-TGAAAACGAAAGAAGTGCGCTGTA--AGTATTACCA
IMP1011-48  CGCCTCCTTGGATACGTCATATC-TGAAAACGAAAGAAGTGCGCTGTA--AGTATTACCA
            **********  *******  *  * ***  **************        *******

PCVPK-15    GCGCACTTCGGCAGCGGCAGCACCTCGGCAGCG--TCAGTG--AAAATGCCAAGCAAGAA
IMP999-ECO  GCGCACTTCGGCAGCGGCAGCACCTCGGCAGCACCTCAGCAGCAACATGCCCAGCAAGAA
IMP1010-ST  GCGCACTTCGGCAGCGGCAGCACCTCGGCAGCACCTCAGCAGCAACATGCCCAGCAAGAA
IMP1011-48  GCGCACTTCGGCAGCGGCAGCACCTCGGCAGCACCTCAGCAGCAACATGCCCAGCAAGAA
IMP1011-48  GCGCACTTCGGCAGCGGCAGCACCTCGGCAGCACCTCAGCAGCAACATGCCCAGCAAGAA
            *********************************    *      **  ** *********
```

Figure No. 5 (continuation)

```
PCVPK-15      ---------AAGCGGCCCGCAACCCCATAAGAGGTGGGTGTTCACCCTTAATAATCCTTC
IMP999-ECO    GAATGGAAGAAGCGGACCCCAACCACATAAAAGGTGGGTGTTCACGCTGAATAATCCTTC
IMP1010-ST    GAATGGAAGAAGCGGACCCCAACCACATAAAAGGTGGGTGTTCACGCTGAATAATCCTTC
IMP1011-48    GAATGGAAGAAGCGGACCCCAACCCCATAAAAGGTGGGTGTTCACTCTGAATAATCCTTC
IMP1011-48    GAATGGAAGAAGCGGACCCCAACCCCATAAAAGGTGGGTGTTCACTCTGAATAATCCTTC
                      ***** ** ***** *****  ************** ** ***********

PCVPK-15      CGAGGAGGAGAAAAACAAAATACGGGAGCTTCCAATCTCCCTTTTTGATTATTTTGTTTG
IMP999-ECO    CGAAGACGAGCGCAAGAAAATACGGGAGCTCCCAATCTCCCTATTTGATTATTTTATTGT
IMP1010-ST    CGAAGACGAGCGCAAGAAAATACGGGAGCTCCCAATCTCCCTATTTGATTATTTTATTGT
IMP1011-48    CGAAGACGAGCGCAAGAAAATACGGGATCTTCCAATATCCCTATTTGATTATTTTATTGT
IMP1011-48    CGAAGACGAGCGCAAGAAAATACGGGATCTTCCAATATCCCTATTTGATTATTTTATTGT
              ***  ** ***    ** *********  ** ****  ***** **** *********  **

PCVPK-15      CGGAGAGGAAGGTTTGGAAGAGGGTAGAACTCCTCACCTCCAGGGGTTTGCGAATTTTGC
IMP999-ECO    TGGCGAGGAGGGTAATGAGGAAGGACGAACACCTCACCTCCAGGGGTTCGCTAATTTTGT
IMP1010-ST    TGGCGAGGAGGGTAATGAGGAAGGACGAACACCTCACCTCCAGGGGTTCGCTAATTTTGT
IMP1011-48    TGGCGAGGAGGGTAATGAGGAAGGACGAACACCTCACCTCCAGGGGTTCGCTAATTTTGT
IMP1011-48    TGGCGAGGAGGGTAATGAGGAAGGACGAACACCTCACCTCCAGGGGTTCGCTAATTTTGT
                ** *****  ***   ** ** **   ****  ******************  ******

PCVPK-15      TAAGAAGCAGACTTTTAACAAGGTGAAGTGGTATTTTGGTGCCCGCTGCCACATCGAGAA
IMP999-ECO    GAAGAAGCAAACTTTTAATAAAGTGAAGTGGTATTTGGGTGCCCGCTGCCACATCGAGAA
IMP1010-ST    GAAGAAGCAAACTTTTAATAAAGTGAAGTGGTATTTGGGTGCCCGCTGCCACATCGAGAA
IMP1011-48    GAAGAAGCAGACTTTTAATAAAGTGAAGTGGTATTTGGGTGCCCGCTGCCACATCGAGAA
IMP1011-48    GAAGAAGCAGACTTTTAATAAAGTGAAGTGGTATTTGGGTGCCCGCTGCCACATCGAGAA
               ******* ******** **  ************** ************************

PCVPK-15      AGCGAAAGGAACCGACCAGCAGAATAAAGAATACTGCAGTAAAGAAGGCCACATACTTAT
IMP999-ECO    AGCCAAAGGAACTGATCAGCAGAATAAAGAATATTGCAGTAAAGAAGGCAACTTACTTAT
IMP1010-ST    AGCCAAAGGAACTGATCAGCAGAATAAAGAATATTGCAGTAAAGAAGGCAACTTACTTAT
IMP1011-48    AGCGAAAGGAACAGATCAGCAGAATAAAGAATACTGCAGTAAAGAAGGCAACTTACTGAT
IMP1011-48    AGCGAAAGGAACAGATCAGCAGAATAAAGAATACTGCAGTAAAGAAGGCAACTTACTGAT
              ***  *******  **  **************** ****************  ** ****  **

PCVPK-15      CGAGTGTGGAGCTCCGCGGAACCAGGGGAAGCGCAGCGACCTGTCTACTGCTGTGAGTAC
IMP999-ECO    TGAATGTGGAGCTCCTCGATCTCAAGGACAACGGAGTGACCTGTCTACTGCTGTGAGTAC
IMP1010-ST    TGAATGTGGAGCTCCTCGATCTCAAGGACAACGGAGTGACCTGTCTACTGCTGTGAGTAC
IMP1011-48    GGAGTGTGGAGCTCCTAGATCTCAGGGACAACGGAGTGACCTGTCTACTGCTGTGAGTAC
IMP1011-48    GGAGTGTGGAGCTCCTAGATCTCAGGGACAACGGAGTGACCTGTCTACTGCTGTGAGTAC
               ** ************  *   ** **  **  *  ** ********************

PCVPK-15      CCTTTTGGAGACGGGGTCTTTGGTGACTGTAGCCGAGCAGTTCCCTGTAACGTATGTGAG
IMP999-ECO    CTTGTTGGAGAGCGGGAGTCTGGTGACCGTTGCAGAGCAGCACCCTGTAACGTTTGTCAG
IMP1010-ST    CTTGTTGGAGAGCGGGAGTCTGGTGACCGTTGCAGAGCAGCACCCTGTAACGTTTGTCAG
IMP1011-48    CTTGTTGGAGAGCGGGAGTCTGGTGACCGTTGCAGAGCAGCACCCTGTAACGTTTGTCAG
IMP1011-48    CTTGTTGGAGAGCGGGAGTCTGGTGACCGTTGCAGAGCAGCACCCTGTAACGTTTGTCAG
              *  *******    ***    *  ******* **  ******    ************** *** **

PCVPK-15      AAATTTCCGCGGGCTGGCTGAACTTTTGAAAGTGAGCGGGAAGATGCAGCAGCGTGATTG
IMP999-ECO    AAATTTCCGCGGGCTGGCTGAACTTTTGAAAGTGAGCGGGAAAATGCAGAAGCGTGATTG
IMP1010-ST    AAATTTCCGCGGGCTGGCTGAACTTTTGAAAGTGAGCGGGAAAATGCAGAAGCGTGATTG
IMP1011-48    AAATTTCCGCGGGCTGGCTGAACTTTTGAAAGTGAGCGGGAAAATGCAGAAGCGTGATTG
IMP1011-48    AAATTTCCGCGGGCTGGCTGAACTTTTGAAAGTGAGCGGGAAAATGCAGAAGCGTGATTG
              ****************************************** ******  *********
```

Figure No. 5 (continuation)

```
PCVPK-15     GAAGACAGCTGTACACGTCATAGTGGGCCCGCCCGGTTGTGGGAAGAGCCAGTGGGCCCG
IMP999-ECO   GAAGACCAATGTACACGTCATTGTGGGGCCACCTGGGTGTGGTAAAAGCAAATGGGCTGC
IMP1010-ST   GAAGACCAATGTACACGTCATTGTGGGGCCACCTGGGTGTGGTAAAAGCAAATGGGCTGC
IMP1011-48   GAAGACTAATGTACACGTCATTGTGGGGCCACCTGGGTGTGGTAAAAGCAAATGGGCTGC
IMP1011-48   GAAGACTAATGTACACGTCATTGTGGGGCCACCTGGGTGTGGTAAAAGCAAATGGGCTGC
             ******   ************  *****  **  **  *****  **  ***  *  *****

PCVPK-15     TAATTTTGCTGAGCCTAGGGACACCTACTGGAAGCCTAGTAGAAATAAGTGGTGGGATGG
IMP999-ECO   TAATTTTGCAGACCCGGAAACCACATACTGGAAACCACCTAGAAACAAGTGGTGGGATGG
IMP1010-ST   TAATTTTGCAGACCCGGAAACCACATACTGGAAACCACCTAGAAACAAGTGGTGGGATGG
IMP1011-48   TAATTTTGCAGACCCGGAAACCACATACTGGAAACCACCTAGAAACAAGTGGTGGGATGG
IMP1011-48   TAATTTTGCAGACCCGGAAACCACATACTGGAAACCACCTAGAAACAAGTGGTGGGATGG
             ********* **  **          ***  ********* **       ******  ************

PCVPK-15     ATATCATGGAGAAGAAGTTGTTGTTTTGGATGATTTTTATGGCTGGTTACCTTGGGATGA
IMP999-ECO   TTACCATGGTGAAGAAGTGGTTGTTATTGATGACTTTTATGGCTGGCTGCCGTGGGATGA
IMP1010-ST   TTACCATGGTGAAGAAGTGGTTGTTATTGATGACTTTTATGGCTGGCTGCCGTGGGATGA
IMP1011-48   TTACCATGGTGAAGAAGTGGTTGTTATTGATGACTTTTATGGCTGGCTGCCCTGGGATGA
IMP1011-48   TTACCATGGTGAAGAAGTGGTTGTTATTGATGACTTTTATGGCTGGCTGCCCTGGGATGA
             **  *****  ********  ******  *  *****  ***********  *  ** *******

PCVPK-15     TCTACTGAGACTGTGTGACCGGTATCCATTGACTGTAGAGACTAAAGGGGGTACTGTTCC
IMP999-ECO   TCTACTGAGACTGTGTGATCGATATCCATTGACTGTAGAGACTAAAGGTGGAACTGTACC
IMP1010-ST   TCTACTGAGACTGTGTGATCGATATCCATTGACTGTAGAGACTAAAGGTGGAACTGTACC
IMP1011-48   TCTACTGAGACTGTGTGATCGATATCCATTGACTGTAGAGACTAAAGGTGGAACTGTACC
IMP1011-48   TCTACTGAGACTGTGTGATCGATATCCATTGACTGTAGAGACTAAAGGTGGAACTGTACC
             ******************  **  *******************************  *****  **

PCVPK-15     TTTTTTGGCCCGCAGTATTTTGATTACCAGCAATCAGGCCCCCCAGGAATGGTACTCCTC
IMP999-ECO   TTTTTTGGCCCGCAGTATTCTGATTACCAGCAATCAGACCCCGTTGGAATGGTACTCCTC
IMP1010-ST   TTTTTTGGCCCGCAGTATTCTGATTACCAGCAATCAGACCCCGTTGGAATGGTACTCCTC
IMP1011-48   TTTTTTGGCCCGCAGTATTCTGATTACCAGCAATCAGACCCCGTTGGAATGGTACTCCTC
IMP1011-48   TTTTTTGGCCCGCAGTATTCTGATTACCAGCAATCAGACCCCGTTGGAATGGTACTCCTC
             *******************  ******************  ****       ***************

PCVPK-15     AACTGCTGTCCCAGCTGTAGAAGCTCTCTATCGGAGGATTACTACTTTGCAATTTTGGAA
IMP999-ECO   AACTGCTGTCCCAGCTGTAGAAGCTCTCTATCGGAGGATTACTTCCTTGGTATTTTGGAA
IMP1010-ST   AACTGCTGTCCCAGCTGTAGAAGCTCTCTATCGGAGGATTACTTCCTTGGTATTTTGGAA
IMP1011-48   AACTGCTGTCCCAGCTGTAGAAGCTCTTTATCGGAGGATTACTTCCTTGGTATTTTGGAA
IMP1011-48   AACTGCTGTCCCAGCTGTAGAAGCTCTTTATCGGAGGATTACTTCCTTGGTATTTTGGAA
             ***************************  **************  *  ***  ********

PCVPK-15     GACTGCTGGAGAACAATCCACGGAGGTACCCGAAGGCCGATTTGAAGCAGTGGACCCACC
IMP999-ECO   GAATGCTACAGAACAATCCACGGAGGAA---GGGGGCCAGTTCGTCACCCTTTCCCCCCC
IMP1010-ST   GAATGCTACAGAACAATCCACGGAGGAA---GGGGGCCAGTTCGTCACCCTTTCCCCCCC
IMP1011-48   GAATGCTACAGAACAATCCACGGAGGAA---GGGGGCCAGTTCGTCACCCTTTCCCCCCC
IMP1011-48   GAATGCTACAGAACAATCCACGGAGGAA---GGGGGCCAGTTCGTCACCCTTTCCCCCCC
             **  ****  *************** *   *   ****  **  *   *   **  **

PCVPK-15     CTGTGCCCTTTTCCCATATAAAATAAATTACTGAGTCTTTTTTGTTATCACATCGTAATG
IMP999-ECO   ATGCCCTGAATTTCCATATGAAATAAATTACTGAGTCTTTTT---TATCACTTCGTAATG
IMP1010-ST   ATGCCCTGAATTTCCATATGAAATAAATTACTGAGTCTTTTT---TATCACTTCGTAATG
IMP1011-48   ATGCCCTGAATTTCCATATGAAATAAATTACTGAGTCTTTTT---TATCACTTCGTAATG
IMP1011-48   ATGCCCTGAATTTCCATATGAAATAAATTACTGAGTCTTTTT---TATCACTTCGTAATG
             **  *    **  ******  *********************         ******  ********
```

Figure No. 5 (continuation and end)

```
PCVPK-15     GTTTTTATT-TTTATTTA---TTTA----GAGGGTCTTTTAGGATAAAATTCTCTGAATTG
IMP999-ECO   GTTTTTATTATTCATTTAGGGTTTAAGTGGGGGGTCTTTAAGATTAAATTCTCTGAATTG
IMP1010-ST   GTTTTTATTATTCATTTAGGGTTTAAGTGGGGGGTCTTTAAGATTAAATTCTCTGAATTG
IMP1011-48   GTTTTTATTATTCATTAAGGGTT-AAGTGGGGGGTCTTTAAGATTAAATTCTCTGAATTG
IMP1011-48   GTTTTTATTATTCATTAAGGGTT-AAGTGGGGGGTCTTTAAGATTAAATTCTCTGAATTG
             ********* ** ***  *    **  *    * ******* **  *******************

PCVPK-15     TACATAAATAGTCAGCCTTACCACATAATTTTGGGCTGTGGCTGC-ATTTTGGAGCGCAT
IMP999-ECO   TACATACATGGTTACACGGATATTGTAGTCCTGG-TCGTATATACTGTTTTCGAACGCAG
IMP1010-ST   TACATACATGGTTACACGGATATTGTAGTCCTGG-TCGTATTTACTGTTTTCGAACGCAG
IMP1011-48   TACATACATGGTTACACGGATATTGTATTCCTGG-TCGTATATACTGTTTTCGAACGCAG
IMP1011-48   TACATACATGGTTACACGGATATTGTATTCCTGG-TCGTATATACTGTTTTCGAACGCAG
             ****** ** **  *  *    ** *  *** **    *  *    **** ** ****

PCVPK-15     AGCCGAGGCCTGTGTGCTCGACATTGGTGTGGGTATTTAAATGGAGCCACAGCTGGTTTC
IMP999-ECO   TGCCGAGGCCTACGTGGTCCACATTTCTAGAGGTTTGTAGCCTCAGCCAAAGCTGATTCC
IMP1010-ST   CGCCGAGGCCTACGTGGTCCACATTTCCAGAGGTTTGTAGTCTCAGCCAAAGCTGATTCC
IMP1011-48   TGCCGAGGCCTACGTGGTCTACATTTCCAGCAGTTTGTAGTCTCAGCCACAGCTGGTTTC
IMP1011-48   TGCCGAGGCCTACGTGGTCTACATTTCCAGTAGTTTGTAGTCTCAGCCACAGCTGATTTC
              ********** *** *** *****    ** *** **** *  ** ***** ** * *

PCVPK-15     TTTTATTATTTGGGTGGAACCAATCAATTGTTTGGTCCAGCTCAGGTTTGGGGGTGAAGT
IMP999-ECO   TTTTGTTATTTGGTTGGAAGTAATCAATAGTGGAGTCAAGAACAGGTTTGGGTGTGAAGT
IMP1010-ST   TTTTGTTATTTGGTTGGAAGTAATCAATAGTGGAGTCAAGAACAGGTTTGGGTGTGAAGT
IMP1011-48   TTTTGTTGTTTGGTTGGAAGTAATCAATAGTGGAATCTAGGACAGGTTTGGGGGTAAAGT
IMP1011-48   TTTTGTTGTTTGGTTGGAAGTAATCAATAGTGGAATCTAGGACAGGTTTGGGGGTAAAGT
             **** ** ***** ******  *******  **  **    ********** ** ****

PCVPK-15     ACCTGGAGTGGTAGGTAAAGGGCTGCCTTATGGTGTGGCGGGAGGAGTAGTTAATATAGG
IMP999-ECO   AACGGGAGTGGTAGGAGAAGGGTTGGGGGATTGTATGGCGGGAGGAGTAGTTTACATATG
IMP1010-ST   AACGGGAGTGGTAGGAGAAGGGTTGGGGGATTGTATGGCGGGAGGAGTAGTTTACATATG
IMP1011-48   AGCGGGAGTGGTAGGAGAAGGGCTGGGTTATGGTATGGCGGGAGGAGTAGTTTACATAGG
IMP1011-48   AGCGGGAGTGGTAGGAGAAGGGCTGGGTTATGGTATGGCGGGAGGAGTAGTTTACATAGG
             *  * ********  *****  **    ** ** ** ** **********  *** *

PCVPK-15     GGTCATAGGCCAAGTTGGTGGAGGGGGTTACAAAGTTGGCATCCAAGATAACAACAGTGG
IMP999-ECO   GGTCATAGGTTAGGGCTGTGGCCTTTGTTACAAAGTTATCATCTAGAATAACAGCAGTGG
IMP1010-ST   GGTCATAGGTTAGGGCTGTGGCCTTTGTTACAAAGTTATCATCTAGAATAACAGCAGTGG
IMP1011-48   GGTCATAGGTGAGGGCTGTGGCCTTTGTTACAAAGTTATCATCTAGAATAACAGCACTGG
IMP1011-48   GGTCATAGGTGAGGGCTGTGGCCTTTGTTACAAAGTTATCATCTAGAATAACAGCACTGG
             ********   *    ****     ***********  *  *****   * ** ***

PCVPK-15     ACCCAACACCTCTTTGATTAGAGGTGATGGGGTCTCTGGGGTAA
IMP999-ECO   AGCCCACTCCCCTATCACCCTGGGTGATGGGGGAGCAGGGCCAG
IMP1010-ST   AGCCCACTCCCCTATCACCCTGGGTGATGGGGGAGCAGGGCCAG
IMP1011-48   AGCCCACTCCCCTGTCACCCTGGGTGATCGGGGAGCAGGGCCAG
IMP1011-48   AGCCCACTCCCCTGTCACCCTGGGTGATCGGGGAGCAGGGCCAG
             * ** ** **  *  *   *   ***** ***  * ***  *
```

Figure No. 6

```
   1  GAATTCAACC TTAACCTTTT TTATTCTGTA gTATTCAAAG GGTATAaAgA
  51  TTTTGTTGGT CCCCCCTCCC GGGGGAACAA AGTCgTCAAT ATTAAATCTC
 101  ATCATGTCCA CCGCCCAGGA GGGCGTTCTG ACTGTGGTAg CCTTGACAgT
 151  ATATCCGAAG GTGCGGGAGA rGCGGGTGTT GAAAATGCCA TTTTTCCTTC
 201  TCCAACGGTA GCGGTGGCGG GGGTGGACmA nCCAcgGGCG GCGGCGGAwG
 251  ATCTGGCCAA GATGGCTGCG GGGCGGTGT CTTCTTCTGC GGTAACGCCT
 301  CCTTGGATAC GTCATAgCTG AAAACGAAAG AAGTGCGCTG TAaGTATTAC
 351  CAGCGCACTT CGGCAGCGGC AGCACCTCGG CAGCaCCTCA GCAGCAACAT
 401  GCCCAGCAAG AAGAATGGAA GAAGCGGACC CCAACCACAT AAAAGGTGGG
 451  TGTTCACGCT GAATAATCCT TCCGAAGACG AGCGCAAGAA AATACGGGAG
 501  CTCCCaATCT CCCTATTTGA TTATTTTATT GTTGGCGAGG AGGGTwwTGA
 551  gGAAnGACgA ACACCTCACC TCCAGGGGTT CGCtAATTTT GTGAAGAAgC
 601  aaACTTtTAA TAAAGTGAAG TGGTATTTGG GTGCCCGCTG CCACATCGAG
 651  AAAGCCAaAG GAACTGATCA GCAGAATAAA GAATATTGCA GTAAAgAAGG
 701  CAACTTACTT ATTGAATGTG GAGCTCCTCG ATCTCAAGGA CAACGGAGTG
 751  ACCTGTCTAC TGCTGTGAGT ACCTTGTTGG AGAGCGGGAG TCTGGTGACC
 801  GTTGCAGAGC AGCACCCTGT AACGTTTGTC AGAAATTTCC GCGGGCTGGC
 851  TGAACTTTTG AAAGTGAGCG GGAAAATGCA GAAGCGTGAT TGGAAGACCA
 901  ATGTACACGT CATTGTGGGG CCACCTGGGT GTGGTAAAAG CAAATGGGCT
 951  GCTAATTTTG CAGACCCGGA AACCACATAC TGGAAACCAC CTAGAAACAA
1001  GTGGTGGGAT GGTTACCATG GTGAAGAAGT GGTTGTTATT GATGACTTTT
1051  ATGGCTGGCT GCCGTGGGAT GATCTACTGA GACTGTGTGA TCGATATCCA
1101  TTGACTGTAG AGACTAAAGG TGGAACTGTA CNNNNNNNGG CCCGCAGTAT
1151  TCTGATTACC AGCAATCAGA CCCCGTtGGA ATGGTACTCC TCAACTGCTG
1201  TCCCAGCtGT AGAAGCTCTC TATCGGAGGA ttACTTCCTT GGTATTTtGG
1251  AaGAATGCTA CAGAACAATC CACGGAGGAA GGGGGCCAGT TnGTCACCCT
```

Figure No. 6 (continuation)

```
1301  TTCCCCCCCA TGCCcTGAAT TTCCATaTGA AATAAATTAC TGAGTCTTTT
1351  TTATCACTTC GTAATGGTTT TTATTATTCA TTTAGGGTTT AAGTGGGGGG
1401  TCTTTAAGAT TAAATTCTCT GAATTGTACA TACATGGTTA CACGGATATT
1451  GTAGTCCTGG TCGTATATAC TGTTTTCGAA CGCAGTGCCG AGGCCTACGT
1501  GGTCCACATT TCTAGAGGTT tGTAGCCTCA gCCAAAGCtG ATTCCTTTTG
1551  TTATTTGGTT GGAAGTAATC AATAGTGGAG TCAAGAACAG GTTTGGGTGT
1601  GAAGTAACGG GAGTGGTAGG AGAAGGGTTG GGGGATTGTA TGGCGGGAGG
1651  AGTAGTTTAC ATATGGGTCA TAGGTTAGGG CTGTGGCCTT TGTTACAAAG
1701  TTATCATcTA GAATAACAGC AGTGGAGCCC ACTCCCTAT CACCCTGGGT
1751  GATGGGGGAG CAGGGCCA
```

Figure No. 7

8con.s = sequence clone pGEM-7/8
pcveco = sequence strain PCV PK/15

SCORES    Init1: 2517 Initn: 3774 Opt: 4010
          75.8% identity in 1785 bp overlap

```
            1769      1759      1749      1739      1729      1719
8con.s  GAATTCTGGCCCTGCTCCCCCATCACCCAGGGTGATAGGGGAGTGGGCTCCACTGCTGTT
        |||||   |   |||  |   ||||||||||     |  |  || || || |||||||| ||||
pcveco  GAATTTTACCCCAGAGACCCCATCACCTCTAATCAAAGAGGTGTTGGGTCCACTGTTGTT
            10        20        30        40        50        60

1709      1699      1689      1679      1669      1659
8con.s  ATTCTAGATGATAACTTTGTAACAAAGGCCACAGCCCTAACCTATGACCCATATGTAAAC
        ||  | ||||  |||||||||||||  |||       ||||   |  ||||||||||| |||  | |||
pcveco  ATCTTGGATGCCAACTTTGTAACCCCCTCCACCAACTTGGCCTATGACCCCTATATTAAC
            70        80        90       100       110       120

1649      1639      1629      1619      1609      1599
8con.s  TACTCCTCCCGCCATACAATCCCCCAACCCTTCTCCTACCACTCCCGTTACTTCACACCC
        ||||||||||||||  || ||   ||  ||||| ||||||||||||||| | |||||||||| |||
pcveco  TACTCCTCCCGCCACACCATAAGGCAGCCCTTTACCTACCACTCCAGGTACTTCACCCCC
           130       140       150       160       170       180

1589      1579      1569      1559      1549      1539
8con.s  AAACCTGTTCTTGACTCCACTATTGATTACTTCCAACCAAATAACAAAAGGAATCAGCTT
        |||||||  || |||   || |||||||||  |||||  ||||||||||| |||||  || |||||
pcveco  AAACCTGAGCTGGACCAAACAATTGATTGGTTCCACCCAAATAATAAAAGAAACCAGCTG
           190       200       210       220       230       240

1529      1519      1509      1499      1489      1479
8con.s  TGGCTGAGGCTACAAACCTCTAGAAATGTGGACCACGTAGGCCTCGGCACTGCGTTCGAA
        |||||       || | |||   |  ||||| || |||    |||||||||||| |||| || ||
pcveco  TGGCTCCATTTAAATACCCACACCAATGTCGAGCACACAGGCCTCGGCTATGCGCTCCAA
           250       260       270       280       290       300

1469      1459      1449      1439      1429      1419
8con.s  AACAGTATATAC-GACCAGGACTACAATATCCGTGTAACCATGTATGTACAATTCAGAGA
        ||  | |    || ||| |||  | |  |   |  || ||  ||||||||||||||||||||
pcveco  AA-TGCAGCCACAGCCCAAAATTATGTGGTAAGGCTGACTATTTATGTACAATTCAGAGA
            310       320       330       340       350

1409      1399      1389      1379      1369      1359
8con.s  ATTTAATCTTAAAGACCCCCCACTTAAACCCTAAATGAATAATAAAAACCATTACGAAGT
        |||||  || ||||||||| |    ||||  |||||| ||  |||||||||||||||||||| ||
pcveco  ATTTATCCTAAAAGACCCTC----TAAA---TAAAT-AAAAATAAAAACCATTACGATGT
        360       370       380       390       400       410

1349      1339      1329      1319      1309      1299
8con.s  GAT---AAAAAAGACTCAGTAATTTATTTCATATGGAAATTCAGGGCATGGGGGGGAAAG
        |||   |||||||||||||||||||||||||| ||||||| ||    | || || |||   |
pcveco  GATAACAAAAAAGACTCAGTAATTTATTTTATATGGGAAAAGGGCACAGGGTGGGTCCAC
          420       430       440       450       460       470
```

Figure No. 7 (continuation)

```
              1289        1279        1269        1259        1249
8con.s  GGTGACNAACTGGCCCCC---TTCCTCCGTGGATTGTTCTGTAGCATTCTTCCAAAATAC
         |  |:||  ||||  |   | |||||||||||||||||  ||||  ||||||||||||
pcveco  TGCTTCAAATCGGCCTTCGGGTACCTCCGTGGATTGTTCTCCAGCAGTCTTCCAAAATTG
              480         490         500         510         520         530

1239        1229        1219        1209        1199        1189
8con.s  CAAGGAAGTAATCCTCCGATAGAGAGCTTCTACAGCTGGGACAGCAGTTGAGGAGTACCA
         ||| |  |||||||||||||||||||||||||||||||||||||||||||||||||||||
pcveco  CAAAGTAGTAATCCTCCGATAGAGAGCTTCTACAGCTGGGACAGCAGTTGAGGAGTACCA
              540         550         560         570         580         590

1179        1169        1159        1149        1139        1129
8con.s  TTCCAACGGGGTCTGATTGCTGGTAATCAGAATACTGCGGGCCNNNNNNNNGTACAGTTCC
         ||||    ||||  |||||||||||||||||  |||||||||||::::::::|  |||||  ||
pcveco  TTCCTGGGGGGCCTGATTGCTGGTAATCAAAATACTGCGGGCCAAAAAAGGAACAGTACC
              600         610         620         630         640         650

1119        1109        1099        1089        1079        1069
8con.s  ACCTTTAGTCTCTACAGTCAATGGATATCGATCACACAGTCTCAGTAGATCATCCCACGG
         |||||||||||||||||||||||||||| ||  ||||||||||||||||||||||||||| ||
pcveco  CCCTTTAGTCTCTACAGTCAATGGATACCGGTCACACAGTCTCAGTAGATCATCCCAAGG
              660         670         680         690         700         710

1059        1049        1039        1029        1019        1009
8con.s  CAGCCAGCCATAAAAGTCATCAATAACAACCACTTCTTCACCATGGTAACCATCCCACCA
         |  ||||||||||||  ||||| |  ||||||  ||||||||  ||||||  ||  |||||||||||
pcveco  TAACCAGCCATAAAAATCATCCAAAACAACAACTTCTTCTCCATGATATCCATCCCACCA
              720         730         740         750         760         770

999         989         979         969         959         949
8con.s  CTTGTTTCTAGGTGGTTTCCAGTATGTGGTTTCCGGGTCTGCAAAATTAGCAGCCCATTT
         ||| |||||||  || |||||||||  |||       || ||  |||||||||    ||||||  |
pcveco  CTTATTTCTACTAGGCTTCCAGTAGGTGTCCCTAGGCTCAGCAAAATTACGGGCCCACTG
              780         790         800         810         820         830

939         929         919         909         899         889
8con.s  GCTTTTACCACACCCAGGTGGCCCCACAATGACGTGTACATTGGTCTTCCAATCACGCTT
         ||| || ||||||  || ||  || ||||||  |||||||||||      |||||||||||||||||
pcveco  GCTCTTCCCACAACCGGGCGGGCCCACTATGACGTGTACAGCTGTCTTCCAATCACGCTG
              840         850         860         870         880         890

879         869         859         849         839         829
8con.s  CTGCATTTTCCCGCTCACTTTCAAAAGTTCAGCCAGCCCGCGGAAATTTCTGACAAACGT
         ||||||  ||||||||||||||||||||||||||||||||||||||||||||||  |||  ||||
pcveco  CTGCATCTTCCCGCTCACTTTCAAAAGTTCAGCCAGCCCGCGGAAATTTCTCACATACGT
              900         910         920         930         940         950

819         809         799         789         779         769
8con.s  TACAGGGTGCTGCTCTGCAACGGTCACCAGACTCCCGCTCTCCAACAAGGTACTCACAGC
         |||||||  ||||||  ||  ||  |||||||| |  |||  |||||||| |  ||||||||||||||
pcveco  TACAGGGAACTGCTCGGCTACAGTCACCAAAGACCCCGTCTCCAAAAGGGTACTCACAGC
              960         970         980         990         1000        1010
```

Figure No. 7 (continuation)

```
          759       749       739       729       719       709
8con.s  AGTAGACAGGTCACTCCGTTGTCCTTGAGATCGAGGAGCTCCACATTCAATAAGTAAGTT
        |||||||||||| || ||  |  || ||    || |||||||||||| || |||||||| ||
pcveco  AGTAGACAGGTCGCTGCGCTTCCCCTGGTTCCGCGGAGCTCCACACTCGATAAGTATGTG
          1020      1030      1040      1050      1060      1070

699       689       679       669       659       649
8con.s  GCCTTCTTTACTGCAATATTCTTTATTCTGCTGATCAGTTCCTTTGGCTTTCTCGATGTG
        ||||||||||||| |||||||||||||||||| |||||||| ||||||||||||||||||
pcveco  GCCTTCTTTACTGCAGTATTCTTTATTCTGCTGGTCGGTTCCTTTCGCTTTCTCGATGTG
          1080      1090      1100      1110      1120      1130

639       629       619       609       599       589
8con.s  GCAGCGGGCACCCAAATACCACTTCACTTTATTAAAAGTTTGCTTCTTCACAAAATTAGC
        |||||||||| |||||||||||||||| || |||||||| ||||||||| |||||||| ||
pcveco  GCAGCGGGCACCAAAATACCACTTCACCTTGTTAAAAGTCTGCTTCTTAGCAAAATTCGC
          1140      1150      1160      1170      1180      1190

579       569       559       549       539       529
8con.s  GAACCCCTGGAGGTGAGGTGTTCGTCNTTCCTCAWWACCCTCCTCGCCAACAATAAAATA
         |||||||||||||||||| ||||   |: || ||  :::||| ||||| ||   || ||||||
pcveco  AAACCCCTGGAGGTGAGGAGTTCTACCCTCTTCCAAACCTTCCTCTCCGCAAACAAAATA
          1200      1210      1220      1230      1240      1250

519       509       499       489       479       469
8con.s  ATCAAATAGGGAGATTGGGAGCTCCCGTATTTTCTTGCGCTCGTCTTCGGAAGGATTATT
        ||||||  ||||||||||| |||||||||||||| ||  ||| || ||||||||||||||
pcveco  ATCAAAAAGGGAGATTGGAAGCTCCCGTATTTTGTTTTTCTCCTCCTCGGAAGGATTATT
          1260      1270      1280      1290      1300      1310

459       449       439       429       419       409
8con.s  CAGCGTGAACACCCACCTTTTATGTGGTTGGGGTCCGCTTCTTCCATTCTTCTTGCTGGG
         || |||||||||||||| |||||  ||||| ||  ||||||       |||||||| ||
pcveco  AAGGGTGAACACCCACCTCTTATGGGGTTGCGGGCCGCTT---------TTCTTGCTTGG
          1320      1330      1340      1350               1360

399       389       379       369       359       349
8con.s  CATGTTGCTGCTGAGGTGCTGCCGAGGTGCTGCCGCTGCCGAAGTGCGCTGGTAATACT-
        ||| ||  ||||    ||||||||||||||||||||||||||||||||||||||||||
pcveco  CATTTT--CACTGA--CGCTGCCGAGGTGCTGCCGCTGCCGAAGTGCGCTGGTAATACTA
          1370      1380      1390      1400      1410

339       329       319       309       299       289
8con.s  -TACAGCGCACTTCTTTC-GTTTTCAGCTATGACGTATCCAAGGAGGCGTTACCGCAGAA
         ||||||||||||||||   ||||      |||||||  ||||||||||||||||||||||||
pcveco  CAGCAGCGCACTTCTTTCACTTTTTATAGAATGACGTGGCCAAGGAGGCGTTACCGCAGAA
          1420      1430      1440      1450      1460      1470

279       269       259       249       239       229
8con.s  GAAGACACCGCCCCCGCAGCCATCTTGGCCAGATCWTCCGCCGCCGCCCGTGGNTKGTCC
        ||||   |||||||||||||||||||| | ||| ||||  |  | || |  :|:| |
pcveco  GAAGGACCCGCCCCCGCAGCCATCTTGGAAACATCCTCCGGAGAAGACCATATTTGGCAC
          1480      1490      1500      1510      1520      1530
```

Figure No. 7 (continuation and end)

```
          219            209          199         189        179
8con.s  ACCCCCGCC-------ACCGCTACCGTTGGAGAAGGAAAAATGGCATTTTCAACACCCGC
        | |||||||       |||| ||| | ||| |  | ||| | || || |||||  |||||
pcveco  A-CCCCGCCTTCAGAAACCGTTACAGATGGCGCCGAAAGACGGGTATCTTCAATTCCCGC
        1540       1550      1560      1570      1580      1590

169        159         149        139        129         119
8con.s  YTCTCCCGCACCTTCGGATATACTGTCAAGGCTACCACAGTCAGAACGCCCTCCTGGGCG
        :| ||       |||| |   || | |||| |   | | || |  ||| || |||
pcveco  CTTTCTACAGAATTTGTACTCACCATAAAAG-GAGGATACTCGCA--GCCATCTTGGAAT
        1600      1610      1620      1630      1640       1650

109        99         89         79         69         59
8con.s  GTGGACATGATGAGATTTAATATTGACGACTTTGTTCCCCCGGGAGGGGGGACCAACAAA
        || ||     | | ||| || || | |  ||  | |||||   ||| || ||||||
pcveco  GTTAACTACCTCAAATTCAACATCGGCCAGTTCCTCCCCCCCTCAGGCGGCACCAACCCC
        1660      1670      1680      1690      1700      1710

49         39         29         19          9
8con.s  ATCTTTATACCCTTTGAATACTACAGAATAAAAAAGGTTAAGGTT
        |    |||| ||  ||||||||| | || | ||||| |||    |
pcveco  CTACCCCTACCTTTCCAATACTACCGTATTAGAAAGGCTAAATAT
        1720      1730      1740      1750
```

PORCINE CIRCOVIRUS VACCINE AND DIAGNOSTICS REAGENTS

The present invention relates to new porcine circovirus (PCV for Porcine CircoVirus) strains responsible for the PMWS syndrome (Porcine Multisystemic Wasting Syndrome also called Post-Weaning Multisystemic Wasting Syndrome) to reagents and methods allowing their detection, to methods of vaccination and to vaccines, as well as to methods of producing these reagents and vaccines.

PCV was originally detected as a noncytopathogenic contaminant in pig kidney cell lines PK/15. This virus was classified among the Circoviridae with the chicken anaemia virus (CAV for Chicken Anaemia Virus) and the PBFDV virus (Pscittacine Beak and Feather Disease Virus). It is a small nonenveloped virus (from 15 to 24 nm) whose common characteristic is to contain a genome in the form of a circular single-stranded DNA of 1.76 to 2.31 kb. It was first thought that this genome encoded a polypeptide of about 30 kDa (Todd et al., Arch Virol 1991, 117; 129–135). Recent work has however shown a more complex transcription (Meehan B. M. et al., 1997, 78; 221–227). Moreover, no significant homologies in nucleotide sequence or in common antigenic determinants are known between the three types of circoviruses known.

The PCV derived from the PK/15 cells is considered not to be pathogenic. Its sequence is known from B. M. Meehan et al., J. Gen. Virol 1997 (78) 221–227. It is only very recently that some authors have thought that strains of PCV could be pathogenic and associated with the PMWS syndrome (Gupi P. S. Nayar et al., Can. Vet. J, vol. 38, 1997: 385–387 and Clark E. G., Proc. Am. Assoc. Swine Prac. 1997; 499–501). Nayar et al. have detected PCV DNA in pigs having the PMWS syndrome using PCR techniques. No wild-type PCV strain has however been isolated and purified so far.

The PMWS syndrome detected in Canada, the United States and France is clinically characterized by a gradual loss of weight and by manifestations such as tachypnea, dyspnea and jaundice. From the pathological point of view, it is manifested by lymphocytic or granulomateus infiltrations, lymphadenopathies and, more rarely, by hepatitis and lymphocytic or granulomateus nephritis (Clark E. G., Proc. Am. Assoc. Swine Prac. 1997; 499–501; La Semaine Vétérinaire No. 26, supplement to La Semaine Vétérinaire 1996 (834); La Semaine Vétérinaire 1997 (857): 54; Gupi P. S. Nayar et al., Can. Vet. J, vol. 38, 1997; 385–387).

The applicant has succeeded in isolating five new PCV strains from pulmonary or ganglionic samples obtained from farms situated in Canada, the United States (California) and France (Brittany), hereinafter called circoviruses according to the invention. These viruses have been detected in lesions in pigs with the PMWS syndrome, but not in healthy pigs.

The applicant has, in addition, sequenced the genome of four of these strains, namely the strains obtained from Canada and the United States as well as two French strains. The strains exhibit a very strong homology with each other at the nucleotide level, exceeding 96% and much weaker with the PK/15 strain, about 76%. The new strains can thus be considered as being representative of a new type of porcine circovirus, called here type II, type I being represented by PK/15.

The subject of the present invention is therefore the group II porcine circovirus, as defined above, isolated or in the form of a purified preparation.

The invention relates to any porcine circovirus capable of being isolated from a physiological sample or from a tissue sample, especially lesions, from a diseased pig having the PMWS syndrome, especially following the method described in the examples, in particular type II circovirus.

The subject of the present invention is more particularly purified preparations of five strains, which were deposited at the ECACC (European Collection of Cell Cultures, Centre for Applied Microbiology & Research, Porton Down, Salisbury, Wiltshire SP4 0JG, United Kingdom) on Thursday Oct. 2, 1997:

provisional accession No. V97100219 (called here Imp. 1008PCV)

provisional accession No. V9700218 (called here Imp. 1010PCV)

provisional accession No. V97100217 (called here Imp. 999PCV), and, on Friday Jan. 16 1998:

provisional accession No. V98011608 (called here Imp. 1011–48285)

provisional accession No. V98011609 (called here Imp. 1011–48121).

The invention aims to consider the porcine circoviruses isolated from a diseased pig and/or the circoviruses having a significant serological similarity with the strains of the invention and/or the circoviruses having cross-hybridization with the strains of the invention under stringency conditions such that there is no hybridization with the PCV PK/15 strain.

The viral strains isolated from a physiological sample or from a tissue sample, especially a lesion, from a pig having the PMWS syndrome can be advantageously propagated on cell lines such as especially pig kidney cell lines, in particular PK/15 cells free from contamination (in particular for PCV, as well as for pestiviruses, porcine adenoviruses and porcine parvoviruses) for their multiplication or specifically for the production of antigen, whole (e.g. virus) and/or subunits (e.g. polypeptides).

Very remarkably and unexpectedly, these isolates have proved very productive in culture on PK/15 cells, which have undeniable advantages for the production of virus or antigen, in particular for the production of inactivated vaccine.

The subject of the present invention is also the preparations of circoviruses isolated after passages on cells, especially cell lines, e.g. PK/15 cells, cultured in vitro while being infected with at least one of the circoviruses according to the invention or of any porcine circovirus capable of being isolated form a physiological sample or from a tissue sample, especially lesions, from a pig having the PMWS syndrome. Its subject is also the culture extract or supernatant, optionally purified by standard techniques, and in general any antigenic preparation obtained from in vitro cultures.

The subject of the invention is also the immunogenic active ingredients and the vaccines containing at least one antigen as defined above.

They may be immunogenic active ingredients based on attenuated live whole viruses, or vaccines prepared with these active ingredients, the attenuation being carried out according to the customary methods, e.g. by passage on cells, preferably by passage on pig cells, especially lines, such as PK/15 cells (for example from 50 to 150, especially of the order of 100, passages). These vaccines comprise in general a vehicle or diluent acceptable from the veterinary point of view, optionally an adjuvant acceptable from the veterinary point of view, as well as optionally a freeze-drying stabilizer.

These vaccines will preferably comprise from $10^3$ to $10^6$ TCID50.

They may be immunogenic active ingredients or vaccines based on circovirus antigen according to the invention, in an inactivated state. The vaccine comprises, in addition, a vehicle or a diluent acceptable from the veterinary point of view, with optionally in addition an adjuvant acceptable from the veterinary point of view.

The circoviruses according to the invention, with the fractions which may be present, are inactivated according to techniques known to persons skilled in the art. The inactivation will be preferably carried out by the chemical route, e.g. by exposing the antigen to a chemical agent such as formaldehyde (formalin), paraformaldehyde, β-propiolactone or ethyleneimine or its derivatives. The preferred method of inactivation will be herein the exposure to a chemical agent and in particular to ethyleneimine or to β-propiolactone.

Preferably, the inactivated vaccines according to the invention will be supplemented with adjuvant, advantageously by being provided in the form of emulsions, for example water-in-oil or oil-in-water, according to techniques well known to persons skilled in the art. It will be possible for the adjuvant character to also come from the incorporation of a customary adjuvant compound into the active ingredient.

Among the adjuvants which may be used, there may be mentioned by way of example aluminium hydroxide, the saponines (e.g. Quillaja saponin or Quil A; see Vaccine Design, The Subunit and Adjuvant Approach, 1995, edited by Michael F. Powel and Mark J. Newman, Plennum Press, New-York and London, p.210), Avridine® (Vaccine Design p. 148), DDA (Dimethyldioctadecylammonium bromide, Vaccine Design p. 157), Polyphosphazene (Vaccine Design p. 204), or alternatively oil-in-water emulsions based on mineral oil, squalene (e.g. SPT emulsion, Vaccine Design p. 147), squalene (e.g. MF59, Vaccine Design p. 183), or water-in-oil emulsions based on metabolizable oil (preferably according to WO-A-94 20071) as well as the emulsions described in U.S. Pat. No. 5,422,109. It is also possible to choose combinations of adjuvants, for example Avridine® or DDA combined with an emulsion.

These vaccines will preferably comprise from $10^6$ to $10^8$ TCID50.

The live vaccine adjuvants can be selected from those given for the inactivated vaccine. The emulsions are preferred. To those indicated for the inactivated vaccine, there may be added those described in WO-A-9416681.

As freeze-drying stabilizer, there may be mentioned by way of example SPGA (Bovarnik et al., J. Bacteriology 59, 509, 950), carbohydrates such as sorbitol, mannitol, starch, sucrose, dextran or glucose, proteins such as albumin or casein, derivatives of these compounds, or buffers such as alkali metal phosphates.

The vaccines according to the invention may comprise one or more active ingredients (antigens) of one or more (2 or 3) of the circoviruses according to the invention.

The invention also provides for combining vaccination against the porcine circovirus with a vaccination against other pig pathogens, in particular those which can be associated with the PMWS syndrome. The vaccine according to the invention may therefore comprise another valency corresponding to another pig pathogen.

The applicant has, in addition, obtained the genome of four of the isolates, identified SEQ ID NO: 1 to 4 and optionally 6.

The subject of the present invention is therefore a DNA fragment containing all or part of one of these sequences. It goes without saying that the invention automatically covers the equivalent sequences, that is to say the sequences which do not change the functionality or the strain-specificity of the sequence described or of the polypeptides encoded by this sequence. There will of course be included the sequences differing by degeneracy of the code.

The invention also covers the equivalent sequences in the sense that they are capable of hybridizing with the above sequence under high stringency conditions and/or have a high homology with the strains of the invention and belong to group II defined above.

These sequences and their fragments can be advantageously used for the in vitro or in vivo expression of polypeptides with the aid of appropriate vectors.

In particular, the open reading frames, forming DNA fragments according to the invention, which can be used to this effect have been identified on the genomic sequence of the type II circoviruses. The invention relates to any polypeptide containing at least one of these open reading frames (corresponding amino acid sequence). Preferably, the invention relates to a protein essentially consisting of ORF4, ORF7, ORF10 or ORF13.

For the expression of subunits in vitro, as a means of expression, *E. coli* or a baculovirus will be preferably used (U.S. Pat. No. 4,745,051). The coding sequence(s) or their fragments are integrated into the baculovirus genome (e.g. the baculovirus Autographa californica Nuclear Polyhedrosis Virus AcNPV) and the latter is then propagated on insect cells, e.g. Spodoptera frugiperda Sf9 (deposit ATCC CRL 1711). The subunits can also be produced in eukaryotic cells such as yeasts (e.g. Saccharomyces cerevisiae) or mammalian cells (e.g. CHO, BHK).

The subject of the invention is also the polypeptides which will be produced in vitro by these expression means, and then optionally purified according to conventional techniques. Its subject is also a subunit vaccine comprising at least one polypeptide as thus obtained, or fragment, in a vehicle or diluent acceptable from the veterinary point of view and optionally an adjuvant acceptable from the veterinary point of view.

For the expression in vivo for the purpose of producing recombinant live vaccines, the coding sequence(s) or their fragments are inserted into an appropriate expression vector under conditions allowing the expression of the polypeptide (s). As appropriate vectors, there may be used live viruses, preferably capable of multiplying in pigs, nonpathogenic for pigs (naturally nonpathogenic or rendered as such), according to techniques well known to persons skilled in the art. There may be used in particular pig herpesviruses such as Aujeszky's disease virus, porcine adenovirus, poxviruses, especially vaccinia virus, avipox virus, canarypox virus, swinepox virus. Plasmid DNAs can also be used as vectors (WO-A-90 11092, WO-A-93 19813, WO-A-94 21797, WO-A-95 20660).

The subject of the invention is therefore also the vectors and the recombinant live vaccines or plasmid vaccines (polynucleotide or DNA vaccines) thus prepared, the vaccines comprising, in addition, a vehicle or diluent acceptable from the veterinary point of view.

The subject of the present invention is also a method which makes it possible to induce an immune response in pigs towards circoviruses according to the invention. Its subject is in particular a method of vaccination which is effective in pigs.

This method provides for the administration to pigs, in one or more portions, of a vaccine above. It is also possible to combine several types of the above vaccines in the same vaccination protocol.

This method provides not only for administration to adult pigs, but also to young pigs or to pregnant females. The vaccination of the latter makes it possible to confer passive immunity to the newborns (maternal antibodies).

The invention also offers the possibility of diagnosing the presence of the circoviruses according to the invention in pigs. Its subject is therefore diagnostic tests and methods relating thereto using reagents which will be described below.

Knowledge of the sequences of the different circoviruses makes it possible to define common sequences which make it possible to produce reagents capable of recognizing all the porcine circoviruses known.

Persons skilled in the art will also be able to select fragments of the sequences corresponding to regions exhibiting little or no homology with the corresponding PK/15 circovirus sequence in order to carry out a specific diagnosis.

Sequence alignments make it possible for persons skilled in the art to select a reagent in accordance with their wishes.

A first reagent consists in the DNA sequences disclosed here and their fragments, which will in particular be used as probes or primers in well-known hybridization or PCR (Polymerase Chain Reaction) techniques.

A second reagent consists in the polypeptides encoded by these sequences from the virus or expressed with the aid of a vector (see above), or synthesized by the chemical route according to conventional techniques for peptide synthesis.

A third and fourth reagent consists in respectively polyclonal and monoclonal antibodies which may be produced according to the customary techniques from the virus, the polypeptides or fragments, extracted or encoded by the DNA sequences.

These second, third and fourth reagents may be used in a diagnostic method, a subject of the invention, in which a test is carried out, on a sample of physiological fluid (blood, plasma, serum and the like) or a sample of tissue (ganglia, liver, lungs, kidneys and the like) obtained from a pig to be tested, for the presence of an antigen specific for a circovirus according to the invention, by seeking to detect either the antigen itself, or antibodies directed against this antigen.

The antigens and antibodies according to the invention may be used in any known laboratory diagnostic technique.

However, it will be preferable to use them in techniques which can be used directly in the field by the veterinary doctor, the breeder or the owner of the animal. Persons skilled in the art have available a range of laboratory and field techniques and are therefore in the perfect position to adapt the use of this antigen and/or antibodies as diagnostic reagent(s).

The diagnostic techniques which will be preferably used within the framework of the present invention are Western blotting, immunofluoroescence, ELISA and immunochromatography.

As regards the use of immunochromatography methods, specialists can refer in particular to Robert F. Zurk et al., Clin. Chem. 31/7, 1144–1150 (1985) as well as to patents or patent applications WO-A-88/08 534, WO-A-91/12528, EP-A-291 176, EP-A-299 428, EP-A-291 194, EP-A-284 232, U.S. Pat. No. 5,120,643, U.S. Pat. No. 5,030,558, U.S. Pat. No. 5,266,497, U.S. Pat. No. 4,740,468, U.S. Pat. No. 5,266,497, U.S. Pat. No. 4,855,240, U.S. Pat. No. 5,451,504, U.S. Pat. No. 5,141,850, U.S. Pat. No. 5,232,835 and U.S. Pat. No. 5,238,652.

Accordingly, it is preferably sought to detect specific antibodies in the sample by an indirect test, by competition or by displacement. To do this, the antigen itself is used as diagnostic reagent, or a fragment of this antigen, conserving recognition of the antibodies. The labelling may be advantageously a labelling with peroxidase or a special labelling, preferably with colloidal gold.

It may also be desired to detect the antigen itself in the sample with the aid of a labelled antibody specific for this antigen. The labelling is advantageously as described above.

By antibody specific for the antigen which can be used in particular in competition or displacement or for the detection of the antigen itself, there is understood monoclonal or polyclonal antibodies specific for the antigen, fragments of these antibodies, preferably Fab or F(ab)'$_2$ fragments.

Another feature of the invention is the roduction of polyclonal or monoclonal antibodies specific for the antigen in accordance with the invention, it being possible for these antibodies to then be used in particular as diagnostic reagent for the detection of the antigen in a sample of physiological fluid or in a tissue sample, or even for the detection of antibodies present in such a sample or specimen. The invention also includes the immunologically functional fragments of these antibodies, in particular the F(ab) and F(ab)'$_2$ fragments.

Antibodies can be prepared by the customary techniques. Reference may be made in particular to Antibodies, A Laboratory Manual, 1988, Cold Spring Harbor Laboratory, USA or to J. W. Goding, Monoclonal Antibodies: Principles and Practice, Academic Press Inc., whose contents are incorporated herein by reference.

It will be possible in particular, as is known per se, to carry out the fusion of spleen cells of mice, immunized with the antigen or with at least one of its fragments, with suitable myelomatous cells.

The subject of the invention is also a preparation, preferably pure or partially pure, or even crude, of monoclonal or polyclonal antibodies specific for the antigen, especially mouse or rabbit antibodies.

The present invention also makes it possible to determine epitopes of interest especially on the basis of the DNA sequences described here, whether epitopes of vaccinal interest or epitopes of interest in diagnosis. From the DNA sequence of the genome of the circovirus according to the invention, persons skilled in the art are in a position to determine epitopes according to known methods, for example an appropriate computer program or PEPSCAN. Epitopes are immunodominant regions of proteins and are as such regions exposed at the surface of the proteins. They can therefore be recognized by antibodies and thus be particularly used in the field of diagnosis either for the preparation of antibodies for diagnostic purposes or for the production of corresponding peptides which can be used as diagnostic reagents.

At the very least, an epitope is a peptide having from 8 to 9 amino acids. A minimum of 13 to 25 amino acids is generally preferred.

Persons skilled in the art are therefore in a position, using one or more of these techniques as well as the other available techniques, to find epitopes for using peptides or antibodies for diagnostic purposes.

The subject of the invention is also a diagnostic kit comprising this antigen and/or polyclonal or monoclonal antibodies specific for this antigen. These are in particular diagnostic kits corresponding to the diagnostic techniques described above.

The invention will now be described in greater detail with the aid of nonlimiting exemplary embodiments, taken with reference to the drawing, in which:

FIG. 1: DNA sequence of the genome of the Imp. 1011–48121 strain

FIG. 2: DNA sequence of the genome of the Imp. 1011–48285 strain

FIG. 3: DNA sequence of the genome of the Imp. 999 strain

FIG. 4: DNA sequence of the genome of the Imp. 1010 strain

FIG. 5: Alignment of the 4 sequences according to FIGS. 1 to 4 with the sequence of the PCV PK/15 strain FIG. 6: DNA sequence of the genome of the Imp. 999 strain as defined in the first filing in France on Oct. 3, 1997

FIG. 7: Alignments of the sequence of FIG. 6 with the sequence of the PK/15 strain Sequence listing SEQ ID SEQ ID No: 1 DNA sequence of the genome of the Imp. 1011–48121 strain SEQ ID No: 2 DNA sequence of the genome of the Imp. 1011–48285 strain SEQ ID No: 3 DNA sequence of the genome of the Imp. 999 strain SEQ ID No: 4 DNA sequence of the genome of the Imp. 1010 strain SEQ ID No: 5 DNA sequence of the genome of the PK/15 strain SEQ ID No: 6 DNA sequence of the genome of the Imp. 999 strain as defined in the first filing in France on Oct. 3, 1997.

EXAMPLES

Example 1

Culture and isolation of the porcine circovirus strains

Tissue samples were collected in France, Canada and the USA from lung and lymph nodes of piglets. These piglets exhibited clinical signs typical of the post-weaning multisystemic wasting syndrome. To facilitate the isolation of the viruses, the tissue samples were frozen at −70° C. immediately after autopsy.

For the viral isolation, suspensions containing about 15% tissue sample were prepared in a minimum medium containing Earle's salts (EMEM, BioWhittaker UK Ltd., Wokingham, UK), penicillin (100 IU/ml) and streptomycin (100 µg/ml) (MEM-SA medium), by grinding tissues with sterile sand using a sterile mortar and pestle. This ground preparation was then taken up in MEM-SA, and then centrifuged at 3000 g for 30 minutes at +4° C. in order to harvest the supernatant.

Prior to the inoculation of the cell cultures, a volume of 100 µl of chloroform was added to 2 ml of each supernatant and mixed continuously for 10 minutes at room temperature. This mixture was then transferred to a microcentrifuge tube, centrifuged at 3000 g for 10 minutes, and then the supernatant was harvested. This supernatant was then used as inoculum for the viral isolation experiments.

All the viral isolation studies were carried out on PK/15 cell cultures, known to be uncontaminated with the porcine circovirus (PCV), pestiviruses, porcine adenoviruses and porcine parvoviruses (Allan G. et al Pathogenesis of porcine circovirus experimental infections of colostrum-deprived piglets and examination of pig foetal material. Vet. Microbiol. 1995, 44, 49–64).

The isolation of the porcine circoviruses was carried out according to the following technique:

Monolayers of PK/15 cells were dissociated by trypsinization (with a trypsin-versene mixture) from confluent cultures, and taken up in MEM-SA medium containing 15% foetal calf serum not contaminated by pestivirus (=MEM-G medium) in a final concentration of about 400,000 cells per ml. 10 ml aliquot fractions of this cell suspension were then mixed with 2 ml aliquot fractions of the inocula described above, and the final mixtures were aliquoted in 6 ml volumes in two Falcon flasks of 25 cm². These cultures were then incubated at +37° C. for 18 hours under an atmosphere containing 10% $CO_2$.

After incubation, the culture medium of the semiconfluent monolayers were treated with 300 mM D-glucosamine (Cat # G48175, Sigma-Aldrich Company Limited, Poole, UK) (Tischr I. et al., Arch. Virol., 1987 96 39–57), then incubation was continued for an additional period of 48–72 hours at +37° C. Following this last incubation, one of the two Falcons of each inoculum was subjected to 3 successive freeze/thaw cycles. The PK/15 cells of the remaining Falcon were treated with a trypsin-versene solution, resuspended in 20 ml of MEM-G medium, and then inoculated into 75 cm² Falcons at a concentration of 400,000 cells/ml. The freshly inoculated flasks were then "superinfected" by addition of 5 ml of the corresponding lysate obtained after the freeze/thaw cycles.

Example 2

Preparation of the samples of cell culture for the detection of porcine circoviruses by immunofluorescence or by in situ hybridization A volume of 5 ml of the "superinfected" suspension was collected and inoculated into a Petri dish 55 mm in diameter containing a sterile and fat-free glass coverslip. The cultures in the flasks and on glass coverslips were incubated at +37° C. and treated with glucosamine as described in Example 1. The cultures on glass coverslips were harvested from 24 to 48 hours after the treatment with glucosamine and fixed, either with acetone for 10 minutes at room temperature, or with 10% buffered formaldehyde for 4 hours. Following this fixing, all the glass coverslips were stored at −70° C., on silica gel, before their use for the in situ hybridization studies and the immunocytochemical labelling studies.

Example 3

Techniques for the detection of PCV sequences by in situ hybridization

In situ hybridization was carried out on tissues collected from diseased pigs and fixed with formaldehyde and also on the preparations of cell cultures inoculated for the viral isolation (see Example 2) and fixed on glass coverslips.

Complete genomic probes corresponding to the PK/15 porcine circoviruses (PCV) and to the infectious chicken anaemia virus (CAV) were used. The plasmid pPCV1, containing the replicative form of the PCV genome, cloned in the form of a single 1.7 kilo base pair (kbp) insert (Meehan B. et al. Sequence of porcine circovirus DNA: affinities with plant circoviruses, J. Gen. Virol. 1997, 78, 221–227), was used as specific viral DNA source for PCV. An analogous plasmid, pCAA1, containing the 2.3 kbp replicative form of the avian circovirus CAV was used as negative control. The respective glycerol stocks of the two plasmids were used for the production and purification of the plasmids according to the alkaline lysis technique (Sambrook J. et al. Molecular cloning: A Laboratory Manual. 2nd Edition, Cold Spring Harbor Laboratory, Cold Spring Harbor, N.Y., 1989) so that they are then used as templates for the preparation of the probes. The circovirus probes representative of the complete genomes of PCV and of CAV were produced from the purified plasmids described above (1 µg for each probe) and from hexanucleotide primers at random using a commercial nonradioactive labelling kit ("DIG DNA labelling kit", Boehringer Mannheim, Lewes, UK) according to the supplier's recommendations.

The digoxigenin-labelled probes were taken up in a volume of 50–100 µl of sterile water before being used for the in situ hybridization.

The diseased pig tissue samples, enclosed in paraffin and fixed with formaldehyde, as well as the preparations of infected cell cultures, fixed with formaldehyde, were prepared for the detection of the PCV nucleic acids according to the following technique:

Sections 5 μm thick were cut from tissue blocks enclosed in paraffin, rendered paraffin free, and then rehydrated in successive solutions of alcohol in decreasing concentrations. The tissue sections and the cell cultures fixed with formaldehyde were incubated for 15 minutes and 5 minutes respectively at +37° C. in a 0.5% proteinase K solution in 0.05 M Tris-HCl buffer containing 5 mM EDTA (pH 7.6). The slides were then placed in a 1% glycine solution in autoclaved distilled water, for 30 seconds, washed twice with 0.01 M PBS buffer (phosphate buffered saline) (pH 7.2), and finally washed for 5 minutes in sterile distilled water. They were finally dried in the open air and placed in contact with the probes.

Each tissue/probe preparation was covered with a clean and fat-free glass coverslip, and then placed in an oven at +90° C. for 10 minutes, and then placed in contact with an ice block for 1 minute, and finally incubated for 18 hours at +37° C. The preparations were then briefly immersed in a 2× sodium citrate salt (SSC) buffer (pH 7.0) in order to remove the protective glass coverslips, and then washed twice for 5 minutes in 2×SSC buffer and finally washed twice for 5 minutes in PBS buffer.

After these washes, the preparations were immersed in a solution of 0.1 M maleic acid, 0.15 M NaCl (pH 7.5) (maleic buffer) for 10 minutes, and then incubated in a 1% solution of blocking reagent (Cat #1096176, Boehringer Mannheim UK, Lewis, East Sussex, UK) in maleic buffer for 20 minutes at +37° C.

The preparations were then incubated with a 1/250 solution of an anti-digoxigenin monoclonal antibody (Boehringer Mannheim), diluted in blocking buffer, for 1 hour at +37° C., washed in PBS and finally incubated with a biotinylated anti-mouse immunoglobulin antibody for 30 minutes at +37° C. The preparations were washed in PBS and the endogenous peroxidase activity was blocked by treatment with a 0.5% hydrogen peroxide solution in PBS for 20 minutes at room temperature. The preparations were again washed in PBS and treated with a 3-amino-9-diethylcarbazole (AEC) substrate (Cambridge Bioscience, Cambridge, UK) prepared immediately before use.

After a final wash with tap water, the preparations were counterstained with hematoxylin, "blued" under tap water, and mounted on microscope glass coverslips with a mounting fluid (GVA Mount, Cambridge Bioscience, Cambridge, UK) . The experimental controls included the use of a nonpertinent negative probe (CAV) and of a positive probe (PCV) on samples obtained from diseased pigs and from nondiseased pigs.

Example 4

Technique for the detection of PCV by immunofluorescence

The initial screening of all the cell culture preparations fixed with acetone was carried out by an indirect immunofluorescence technique (IIF) using a 1/100 dilution of a pool of adult pig sera. This pool of sera comprises sera from 25 adult sows from Northern Ireland and is known to contain antibodies against a wide variety of porcine viruses, including PCV: porcine parvovirus, porcine adenovirus, and PRRS virus. The IIF technique was carried out by bringing the serum (diluted in PBS) into contact with the cell cultures for one hour at +37° C., followed by two washes in PBS. The cell cultures were then stained with a 1/80 dilution in PBS of a rabbit anti-pig immunoglobulin antibody conjugated with fluorescein isothiocyanate for one hour, and then washed with PBS and mounted in glycerol buffer prior to the microscopic observation under ultraviolet light.

Example 5

Results of the in situ hybridization on diseased pig tissues

The in situ hybridization, using a PCV genomic probe, prepared from tissues collected from French, Canadian and Californian piglets having multisystemic wasting lesions and fixed with formaldehyde, showed the presence of PCV nucleic acids associated with the lesions, in several of the lesions studied. No signal was observed when the PCV genomic probe was used on tissues collected from nondiseased pigs or when the CAV probe was used on the diseased pig tissues. The presence of PCV nucleic acid was identified in the cytoplasm and the nucleus of numerous mononuclear cells infiltrating the lesions in the lungs of the Californian piglets. The presence of PCV nucleic acid was also demonstrated in the pneumocytes, the bronchial and bronchiolar epithelial cells, and in the endothelial cells of the arterioles, the veinlets and lymphatic vessels.

In diseased French pigs, the presence of PCV nucleic acid was detected in the cytoplasm of numerous follicular lymphocytes and in the intrasinusoidal mononuclear cells of the lymph nodes. The PCV nucleic acid was also detected in occasional syncytia. Depending on these detection results, samples of Californian pig lungs, French pig mesenteric lymph nodes, and Canadian pig organs were selected for the purpose of isolating new porcine circovirus strains.

Example 6

Results of the cell culture of the new porcine circovirus strains and detection by immunofluorescence No cytopathic effect (CPE) was observed in the cell cultures inoculated with the samples collected from French piglets (Imp.1008 strain), Californian piglets (Imp.999 strain) and Canadian piglets (Imp.1010 strain) showing clinical signs of multisystemic wasting syndrome. However, immunolabelling of the preparations obtained from the inoculated cell cultures, after fixing using acetone and with a pool of pig polyclonal sera, revealed nuclear fluorescence in numerous cells in the cultures inoculated using the lungs of Californian piglets (Imp.999 strain), using the mediastinal lymph nodes of French piglets (Imp.1008 strain), and using organs of Canadian piglets (Imp.1010 strain).

Example 7

Extraction of the genomic DNA of the porcine circoviruses

The replicative forms of the new strains of porcine circoviruses (PCV) were prepared using infected PK/15 cell cultures (see Example 1) (10 Falcons of 75 $cm^2$) harvested after 72–76 hours of incubation and treated with glucosamine, as described for the cloning of the replicative form of CAV (Todd. D. et al. Dot blot hybridization assay for chicken anaemia agent using a cloned DNA probe. J. Clin. Microbiol. 1991, 29, 933–939). The double-stranded DNA of these replicative forms was extracted according to a modification of the Hirt technique (Hirt B. Selective extraction of polyoma virus DNA from infected cell cultures, J. Mol. Biol. 1967, 36, 365–369), as described by Molitor (Molitor T. W. et al. Porcine parvovirus DNA: characterization of the genomic and replicative form DNA of two virus isolates, Virology, 1984, 137, 241–254).

Example 8

Restriction map of the replicative form of the genome of the porcine circovirus Imp.999 strain.

The DNA (1–5 μg) extracted according to the Hirt technique was treated with Sl nuclease (Amersh801 am) according to the supplier's recommendations, and then this DNA was digested with various restriction enzymes (Boehringer Mannheim, Lewis, East Sussex, UK) and the products of digestion were separated by electrophoresis on a 1.5% agarose gel in the presence of ethidium bromide as described by Todd et al. (Purification and biochemical characterization of chicken anemia agent. J. Gen. Virol. 1990, 71, 819–823). The DNA extracted from the cultures of the Imp.999 strain possess a unique EcoRI site, 2 SacI sites and do not possess any PstI site. This restriction profile is therefore different from the restriction profile shown by the PCV PK/15 strain (Meehan B. et al. Sequence of porcine circovirus DNA; affinities with plant circoviruses, 1997 78, 221–227) which possess in contrast a PstI site and do not possess any EcoRI site.

Example 9
Cloning of the genome of the porcine circovirus Imp.999 strain

The restriction fragment of about 1.8 kbp generated by digestion of the double-stranded replicative form of the PCV Imp.999 strain with the restriction enzyme EcoRI was isolated after electrophoresis on a 1.5% agarose gel (see Example 3) using a Qiagen commercial kit (QIAEXII Gel Extraction Kit, Cat #20021, QIAGEN Ltd., Crawley, West Sussex, UK). This EcoRI-EcoRI restriction fragment was then ligated with the vector pGEM-7 (Promega, Medical Supply Company, Dublin, Ireland), previously digested with the same restriction enzymes and dephosphorylated, according to standard cloning techniques (Sambrook J. et al. Molecular cloning: A Laboratory Manual, 2nd Edition, Cold Spring Harbor Laboratory, Cold Spring Harbor, N.Y., 1989). The plasmids obtained were transformed into an *Escherichia coli* JM109 host strain (Stratagene, La Jolla, USA) according to standard techniques. The EcoRI-EcoRI restriction fragment of the PCV Imp.999 strain was also cloned into the EcoRI site of the vector pBlueScript SK+ (Stratagene Inc. La Jolla, USA) . Among the clones obtained for each host strain, at least 2 clones containing the fragments of the expected size were selected. The clones obtained were then cultured and the plasmids containing the complete genome of the Imp.999 strain were purified in a small volume (2 ml) or in a large volume (250 ml) according to standard plasmid preparation and purification techniques.

Example 10
Sequencing of a genomic DNA (doublestranded replicative form) of the PCV Imp.999 strain.

The nucleotide sequence of 2 EcoRI Imp.999 clones (clones pGEM-7/2 and pGEM-7/8) was determined according to Sanger's dideoxynucleotide technique using the sequencing kit "AmpliTaq DNA polymerase FS" (Cat #402079 PE Applied Biosystems, Warrington, UK) and an Applied BioSystems AB1373A automatic sequencing apparatus according to the supplier's recommendations. The initial sequencing reactions were carried out with the M13 "forward" and "reverse" universal primers. The following sequencing reactions were generated according to the "DNA walking" technique. The oligonucleotides necessary for these subsequent sequencings were synthesized by Life Technologies (Inchinnan Business Park, Paisley, UK).

The sequences generated were assembled and analysed by means of the MacDNASIS version 3.2 software (Cat #22020101, Appligene, Durham, UK) . The various open reading frames were analysed by means of the BLAST algorithm available on the "National Center for Biotechnology Information" (NCBI, Bethesda, MD, USA) server.

The complete sequence (EcoRI-EcoRI fragment) obtained initially from the clone pGEM-7/8 (SEQ ID No: 6) is presented in FIG. No. 6. It starts arbitrarily after the G of the EcoRI site and exhibits a few uncertainties from the point of view of the nucleotides.

The sequencing was then optimized and the SEQ ID No: 3 (FIG. 3) gives the total sequence of this strain, which was made to start arbitrarily at the beginning of the EcoRI site, that is to say the G as the first nucleotide.

The procedure was carried out in a similar manner for obtaining the sequence of the other three isolates according to the invention (see SEQ ID Nos: 1, 2 and 4 and FIGS. 1, 2 and 4).

The size of the genome of these four strains is:

| | |
|---|---|
| Imp. 1011-48121 | 1767 nucleotides |
| Imp. 1011-48285 | 1767 nucleotides |
| Imp. 999 | 1768 nucleotides |
| Imp. 1010 | 1768 nucleotides |

Example 11
Analysis of the sequence of the PCV Imp.999 strain.

When the sequence generated from the Imp.999 strain was used to test for homology with respect to the sequences contained in the GenBank databank, the only significant homology which was detected is a homology of about 76% (at nucleic acid level) with the sequence of the PK/15 strain (accession numbers Y09921 and U49186) (see FIG. No. 5).

At amino acid level, the test for homology in the translation of the sequences in the 6 phases with the databanks (BLAST X algorithm on the NCBI server) made it possible to demonstrate a 94% homology with the open reading frame corresponding to the theoretical replicase of the BBTV virus similar to the circoviruses of plants (GenBank identification number 1841515) encoded by the GenBank U49186 sequence.

No other sequence contained in the databanks show significant homology with the sequence generated from the PCV Imp.999 strain.

Analysis of the sequences obtained from the Imp.999 strain cultured using lesions collected from Californian piglets having clinical signs of the multisystemic wasting syndrome shows clearly that this viral isolate is a new porcine circovirus strain.

Example 12
Comparative analysis of the sequences

The alignment of the nucleotide sequences of the 4 new PCV strains was made with the sequence of the PCV PK/15 strain (FIG. 5). A homology matrix taking into account the four new strains and the previous PK/15 strain was established. The results are the following:

| | 1 | 2 | 3 | 4 | 5 |
|---|---|---|---|---|---|
| 1 | 1.0000 | 0.9977 | 0.9615 | 0.9621 | 0.7600 |
| 2 | | 1.0000 | 0.9621 | 0.9632 | 0.7594 |
| 3 | | | 1.0000 | 0.9949 | 0.7560 |
| 4 | | | | 1.0000 | 0.7566 |
| 5 | | | | | 1.0000 |

1: Imp. 1011-48121
2: Imp. 1011-48285
3: Imp. 999
4: Imp. 1010
5: PK/15

The homology between the two French strains Imp. 1011–48121 and Imp. 1011–48285 is greater than 99% (0.9977).

The homology between the two North American strains Imp. 999 and Imp. 1010 is also greater than 99% (0.9949). The homology between the French strains and the North American strains is slightly greater than 96%.

The homology between all these strains and PK/15 falls at a value between 75 and 76%.

It is deduced therefrom that the strains according to the invention are representative of a new type of porcine circovirus, distinct from the type represented by the PK/15 strain. This new type, isolated from pigs exhibiting the PMWS syndrome, is called type II porcine circovirus, PK/15 representing type I. The strains belonging to this type II exhibit remarkable nucleotide sequence homogeneity, although they have in fact been isolated from very distant geographical regions.

Example 13

Analysis of the proteins encoded by the genome of the new PCV strains.

The nucleotide sequence of the Imp. 1010 isolate was considered to be representative of the other circovirus strains associated with the multi-systemic wasting syndrome. This sequence was analysed in greater detail with the aid of the BLASTX algorithm (Altschul et al. J. Mol. Biol. 1990. 215. 403–410) and of a combination of programs from the set of MacVector 6.0 software (Oxford Molecular Group, Oxford OX4 4GA, UK). It was possible to detect 13 open reading frames (or ORFs) of a size greater than 20 amino acids on this sequence (circular genome). These 13 ORFs are the following:

| Name | Start | End | Strand | Size of the ORF (nucleotides (nt)) | Protein size (amino acids (aa)) |
|---|---|---|---|---|---|
| ORF1 | 103 | 210 | sense | 108 nt | 35 aa |
| ORF2 | 1180 | 1317 | sense | 138 nt | 45 aa |
| ORF3 | 1363 | 1524 | sense | 162 nt | 53 aa |
| ORF4 | 398 | 1342 | sense | 945 nt | 314 aa |
| ORF5 | 900 | 1079 | sense | 180 nt | 59 aa |
| ORF6 | 1254 | 1334 | sense | 81 nt | 26 aa |
| ORF7 | 1018 | 704 | antisense | 315 nt | 104 aa |
| ORF8 | 439 | 311 | antisense | 129 nt | 42 aa |
| ORF9 | 190 | 101 | antisense | 90 nt | 29 aa |
| ORF10 | 912 | 733 | antisense | 180 nt | 59 aa |
| ORF11 | 645 | 565 | antisense | 81 nt | 26 aa |
| ORF12 | 1100 | 1035 | antisense | 66 nt | 21 aa |
| ORF13 | 314 | 1381 | antisense | 702 nt | 213 aa |

The positions of the start and end of each ORF refer to the sequence presented in FIG. No. 4 (SEQ ID No. 4), of the genome of strain 1010. The limits of ORFs 1 to 13 are identical for strain 999. They are also identical for strains 1011-48121 and 1011-48285, except for the ORFs 3 and 13:

ORF3 1432–1539, sense, 108 nt, 35aa

ORF1,3 314–1377, antisense, 705 nt, 234 aa.

Among these 13 ORFs, 4 have a significant homology with analogous ORFs situated on the genome of the cloned virus PCV PK-15. Each of the open reading frames present on the genome of all the circovirus isolates associated with the multisystemic wasting syndrome was analysed. These 4 ORFs are the following:

| Name | Start | End | Strand | Size of the ORF (nt) | Protein size (aa) | Molecular mass |
|---|---|---|---|---|---|---|
| ORF4 | 398 | 1342 | sense | 945 nt | 314 aa | 37.7 kDa |
| ORF7 | 1018 | 704 | antisense | 315 nt | 104 aa | 11.8 kDa |
| ORF10 | 912 | 733 | antisense | 180 nt | 59 aa | 6.5 kDa |
| ORF13 | 314 | 1381 | antisense | 702 nt | 233 aa | 27.8 kDa |

The positions of the start and end of each ORF refer to the sequence presented in FIG. No. 4 (SEQ ID No. 4). The size of the ORF (in nucleotides=nt) includes the stop codon.

The comparison between the genomic organization of the PCV Imp. 1010 and PCV PK-15 isolates allowed the identification of 4 ORFs preserved in the genome of the two viruses. The table below presents the degrees of homology observed:

| ORF Imp. 1010/ORF PVC PK-15 | Percentage homology |
|---|---|
| ORF4/ORF1 | 86% |
| ORF13/ORF2 | 66.4% |
| ORF7/ORF3 | 61.5% (at the level of the overlap (104 aa)) |
| ORF10/ORF4 | 83% (at the level of the overlap (59 aa)) |

The greatest sequence identity was observed between ORF4 Imp. 1010 and ORF1 PK-15 (86% homology). This was expected since this protein is probably involved in the replication of the viral DNA and is essential for the viral replication (Meehan et al. J. Gen. Virol. 1997. 78. 221–227; Mankertz et al. J. Gen. Virol. 1998. 79. 381–384).

The sequence identity between ORF13 Imp. 1010 and ORF2 PK-15 is less strong (66.4% homology), but each of these two ORFs indeed exhibits a highly conserved N-terminal basic region which is identical to the N-terminal region of the major structural protein of the CAV avian circovirus (Meehan et al. Arch. Virol. 1992. 124. 301–319). Furthermore, large differences are observed between ORF7 Imp. 1010 and ORF3 PK-15 and between ORF10 Imp. 1010 and ORF4 PK-15. In each case, there is a deletion of the C-terminal region of the ORF7 and ORF10 of the Imp. 1010 isolate when they are compared with ORF3 and ORF4 of PCV PK-15. The greatest sequence homology is observed at the level of the N-terminal regions of ORF7/ORF3 (61.5% homology at the level of the overlap) and of ORF10/ORF4 (83% homology at the level of the overlap).

It appears that the genomic organization of the porcine circovirus is quite complex as a consequence of the extreme compactness of its genome. The major structural protein is probably derived from splicing between several reading frames situated on the same strand of the porcine circovirus genome. It can therefore be considered that any open reading frame (ORF1 to ORF13) as described in the table above can represent all or part of an antigenic protein encoded by the type II porcine circovirus and is therefore potentially an antigen which can be used for specific diagnosis and/or for vaccination. The invention therefore relates to any protein comprising at least one of these ORFs. Preferably, the invention relates to a protein essentially consisting of ORF4, ORF7, ORF10 or ORF13.

Example 14
Infectious character of the PCV genome cloned from the new strains.

The plasmid pGEM-7/8 containing the complete genome (replicative form) of the Imp.999 isolate was transfected into PK/15 cells according to the technique described by Meehan B. et al. (Characterization of viral DNAs from cells infected with chicken anemia agent: sequence analysis of the cloned replicative form and transfection capabilities of cloned genome fragments. Arch. Virol. 1992, 124, 301–319). Immunofluorescence analysis (see Example 4) carried out on the first passage after transfection on noncontaminated PK/15 cells have shown that the plasmid of the clone pGEM7/8 was capable of inducing the production of infectious PCV virus. The availability of a clone containing an infectious PCV genetic material allows any useful manipulation on the viral genome in order to produce modified PCV viruses (either attenuated in pigs, or defective) which can be used for the production of attenuated or recombinant vaccines, or for the production of antigens for diagnostic kits.

Example 15
Production of PCV antigens by in vitro culture

The culture of the noncontaminated PK/15 cells and the viral multiplication were carried out according to the same methods as in Example 1. The infected cells are harvested after trypsinization after 4 days of incubation at 37° C. and enumerated. The next passage is inoculated with 400,000 infected cells per ml.

Example 16
Inactivation of the viral antigens

At the end of the viral culture, the infected cells are harvested and lysed using ultrasound (Branson Sonifier) or with the aid of a rotor-stator type colloid mill (UltraTurrax, IKA). The suspension is then centrifuged at 3700 g for 30 minutes. The viral suspension is inactivated with 0.1% ethyleneimine for 18 hours at +37° C. or with 0.5% beta-propiolactone for 24 hours at +28° C. If the virus titre before inactivation is inadequate, the viral suspension is concentrated by ultrafiltration using a membrane with a 300 kDa cut-off (Millipore PTMK300). The inactivated viral suspension is stored at +50° C.

Example 17
Preparation of the vaccine in the form of an emulsion based on mineral oil.

The vaccine is prepared according to the following formula:
 suspension of inactivated porcine circovirus: 250 ml
 Montanide® ISA 70 (SEPPIC): 750 ml The aqueous phase and the oily phase are sterilized separately by filtration. The emulsion is prepared by mixing and homogenizing the ingredients with the aid of a Silverson turbine emulsifier.

One vaccine dose contains about $10^{7.5}$ TCID50. The volume of one vaccine dose is 0.5 ml for administration by the intradermal route, and 2 ml for administration by the intramuscular route.

Example 18
Preparation of the vaccine in the form of a metabolizable oil-based emulsion.

The vaccine is prepared according to the following formula:
 suspension of inactivated porcine circovirus: 200 ml
 Dehymuls HRE 7 (Henkel): 60 ml
 Radia 7204 (Oleofina): 740 ml The aqueous phase and the oily phase are sterilized separately by filtration. The emulsion is prepared by mixing and homogenizing the ingredients with the aid of a Silverson turbine emulsifier.

One vaccine dose contains about $10^{7.5}$ TCID50. The volume of one vaccine dose is 2 ml for administration by the intramuscular route.

Example 19
The indirect immunofluorescence results in relation to the US and French PCV virus strains and to the PK/15 contaminant with a hyperimmune serum (PCV-T), a panel of monoclonal antibodies F99 prepared from PK/15 and a hyperimmune serum prepared from the Canadian strain (PCV-C)

|  | VIRUS | | |
| --- | --- | --- | --- |
|  | PK/15 | USA | France |
| PCV-T antiserum | ≧6400 | 200 | 800 |
| PCV-C antiserum | 200 | ≧6.400 | ≧6.400 |
| F99 1H4 | ≧10000 | <100 | 100 |
| F99 4B10 | ≧10000 | <100 | <100 |
| F99 2B7 | ≧10000 | 100 | <100 |
| F99 2E12 | ≧10000 | <100 | <100 |
| F99 1C9 | ≧10000 | <100 | 100 |
| F99 2E1 | ≧10000 | <100 | <100 |
| F99 1H4 | ≧10000 | 100 | <100 |

Reciprocal of the last dilution of the serum or of the monoclonal antibody which gives a positive reaction in indirect immunofluorescence.

What is claimed is:

1. A vector comprising an isolated DNA molecule comprising a sequence selected from the group consisting of SEQ ID NO: 1,2,3,4 and 6.

2. The vector of claim 1 wherein the DNA molecule comprises SEQ ID NO: 1.

3. The vector of claim 1 wherein the DNA molecule comprises SEQ ID NO: 2.

4. The vector of claim 1 wherein the DNA molecule comprises SEQ ID NO: 3.

5. The vector of claim 1 wherein the DNA molecule comprises SEQ ID NO: 4.

6. The vector of claim 1 wherein the DNA molecule comprises SEQ ID NO: 6.

7. The vector of claim 1 wherein the isolated DNA molecule is expressed by the vector in vivo.

8. The vector of claim 1 wherein the isolated DNA molecule is expressed by the vector in vitro.

9. A vector comprising an isolated DNA molecule comprising a sequence selected from the group consisting of ORFs 1 to 13 of porcine circovirus type II.

10. The vector of claim 9 wherein in the ORF comprises ORF 4.

11. The vector of claim 9 wherein in the ORF comprises ORF 7.

12. The vector of claim 9 wherein in the ORF comprises ORF 10.

13. The vector of claim 9 wherein in the ORF comprises ORF 13.

14. The vector of claim 9, wherein the isolated DNA molecule is expressed by the vector in vivo.

15. The vector of claim 9, wherein the isolated DNA molecule is expressed by the vector in vitro.

16. The vector of any one claims 38–48 wherein the vector is a virus.

17. The vector of claim 16 wherein the virus is selected from the group consisting of pig herpes virus, porcine adenovirus, and poxvirus.

18. An immunogenic composition comprising a vector as claimed in claim 17.

19. The vector of claim 17 wherein the virus is selected form the group consisting of Aujesky's disease virus, vaccinia virus, avipox virus, and swinepox virus.

20. An immunogenic composition comprising a vector as claimed in claim 19.

21. The vector of claim 19 wherein the virus is a canarypox virus.

22. An immunogenic composition comprising a vector as claimed in claim 21.

23. The vector of any one of claims 1,9,2–6, and 10–13 wherein the vector comprises a DNA plasmid.

24. An immunogenic composition comprising a vector as claimed in claim 23.

25. An immunogenic composition comprising a vector as claimed in any one of claims 1,9,2–6, and 10–13.

26. An isolated DNA molecule comprising a sequence selected from the group consisting of SEQ ID NO: 1,2,3,4 and 6.

27. The isolated DNA molecule of claim 26 wherein the DNA molecule comprising SEQ ID NO: 1.

28. The isolated DNA molecule of claim 26 wherein the DNA molecule comprising SEQ ID NO: 2.

29. The isolated DNA molecule of claim 26 wherein the DNA molecule comprising SEQ ID NO: 3.

30. The isolated DNA molecule of claim 26 wherein the DNA molecule comprising SEQ ID NO: 4.

31. The isolated DNA molecule of claim 26 wherein the DNA molecule comprising SEQ ID NO: 6.

32. An isolated DNA molecule comprising a nucleotide sequence encoding an epitope which is specific to PCV-2 and not specific to PCV-1.

33. A vector comprising an isolated DNA molecule as claimed in claim 1.

34. The vector according to claim 33, wherein the isolated DNA molecule is expressed in vivo.

35. The vector according to claim 33, wherein the isolated DNA molecule is expressed in vitro.

* * * * *

UNITED STATES PATENT AND TRADEMARK OFFICE
CERTIFICATE OF CORRECTION

PATENT NO.    : 6,368,601 B1
DATED         : April 9, 2002
INVENTOR(S)   : Gordon Allan et al.

It is certified that error appears in the above-identified patent and that said Letters Patent is hereby corrected as shown below:

<u>Title page,</u>
Item [73], Assignee: change "Lyons" to -- Lyon --

<u>Column 27,</u>
Line 44, change "claims 38-49" to -- claims 1-6 and 9-13 --

<u>Column 28,</u>
Line 43, change "1" to -- 32 --

Signed and Sealed this

Eighth Day of October, 2002

Attest:

JAMES E. ROGAN
*Attesting Officer*   *Director of the United States Patent and Trademark Office*

SEQUENCE LISTING

<160> NUMBER OF SEQ ID NOS: 6

<210> SEQ ID NO 1
<211> LENGTH: 1767
<212> TYPE: DNA
<213> ORGANISM: Porcine circovirus

<400> SEQUENCE: 1
aattcaacct taacctttct tattctgtag tattcaaagg gcacagagcg ggggtttgag    60

-continued

```
cccctcctg ggggaagaaa gtcattaata ttgaatctca tcatgtccac cgcccaggag      120
ggcgttctga ctgtggttcg cttgacagta tatccgaagg tgcgggagag gcgggtgttg      180
aagatgccat ttttccttct ccagcggtaa cggtggcggg ggtggacgag ccaggggcgg      240
cggcggagga tctggccaag atggctgcgg gggcggtgtc ttcttctccg gtaacgcctc      300
cttggatacg tcatatctga aaacgaaaga agtgcgctgt aagtattacc agcgcacttc      360
ggcagcggca gcacctcggc agcacctcag cagcaacatg ccgagcaaga agaatggaag      420
aagcggaccc caaccccata aaggtgggt gttcactctg aataatcctt ccgaagacga      480
gcgcaagaaa atacgggatc ttccaatatc cctatttgat tattttattg ttggcgagga      540
gggtaatgag gaaggacgaa cacctcacct ccagggttc gctaattttg tgaagaagca      600 gactttttaat aaagtgaagt ggtatttggg tgcccgctgc cacatcgaga aagcgaaagg      660
aacagatcag cagaataaag aatactgcag taaagaaggc aacttactga tggagtgtgg      720
agctcctaga tctcagggac aacggagtga cctgtctact gctgtgagta ccttgttgga      780
gagcgggagt ctggtgaccg ttgcagagca gcaccctgta acgtttgtca gaaatttccg      840
cgggctggct gaacttttga aagtgagcgg gaaaatgcag aagcgtgatt ggaagactaa      900
tgtacacgtc attgtgggc cacctgggtg tggtaaaagc aaatgggctg ctaattttgc      960
agacccggaa accacatact ggaaaccacc tagaaacaag tggtgggatg gttaccatgg      1020
tgaagaagtg gttgttattg atgactttta tggctggctg ccctgggatg atctactgag      1080
actgtgtgat cgatatccat tgactgtaga gactaaaggt ggaactgtac cttttttggc      1140
ccgcagtatt ctgattacca gcaatcagac cccgttggaa tggtactcct caactgctgt      1200
cccagctgta gaagctcttt atcggaggat tacttccttg gtattttgga agaatgctac      1260
agaacaatcc acggaggaag ggggccagtt cgtcacccct tccccccat gccctgaatt      1320 tccatatgaa ataaattact gagtcttttt tatcacttcg taatggtttt tattattcat      1380
taagggttaa gtggggggtc tttaagatta aattctctga attgtacata catggttaca      1440
cggatattgt attcctggtc gtatatactg ttttcgaacg cagtgccgag gcctacgtgg      1500
tctacatttc cagcagtttg tagtctcagc cacagctggt ttcttttgtt gtttggttgg      1560
aagtaatcaa tagtggaatc taggacaggt ttggggtaa agtagcggga gtggtaggag      1620
aagggctggg ttatggtatg gcgggaggag tagtttacat aggggtcata ggtgagggct      1680
gtggcctttg ttcaaagtt atcatctaga ataacagcac tggagcccac tcccctgtca      1740
ccctgggtga tcgggagca gggccag                                         1767
```

<210> SEQ ID NO 2
<211> LENGTH: 1767
<212> TYPE: DNA
<213> ORGANISM: Porcine circovirus

<400> SEQUENCE: 2

```
aattcaacct taacctttct tattctgtag tattcaaagg gcacagagcg ggggtttgag       60 cccctcctg ggggaagaaa gtcattaata ttgaatctca tcatgtccac cgcccaggag      120
ggcgttttga ctgtggttcg cttgacagta tatccgaagg tgcgggagag gcgggtgttg      180
aagatgccat ttttccttct ccagcggtaa cggtggcggg ggtggacgag ccaggggcgg      240
cggcggagga tctggccaag atggctgcgg gggcggtgtc ttcttctccg gtaacgcctc      300
cttggatacg tcatatctga aaacgaaaga agtgcgctgt aagtattacc agcgcacttc      360
ggcagcggca gcacctcggc agcacctcag cagcaacatg ccagcaaga agaatggaag      420
```

-continued

```
aagcggaccc caaccccata aaaggtgggt gttcactctg aataatcctt ccgaagacga    480
gcgcaagaaa atacgggatc ttccaatatc cctatttgat tattttattg ttggcgagga    540
gggtaatgag gaaggacgaa cacctcacct ccagggggttc gctaattttg tgaagaagca   600
gacttttaat aaagtgaagt ggtatttggg tgcccgctgc cacatcgaga aagcgaaagg    660
aacagatcag cagaataaag aatactgcag taaagaaggc aacttactga tggagtgtgg    720
agctcctaga tctcagggac aacgagtga cctgtctact gctgtgagta ccttgttgga    780
gagcgggagt ctggtgaccg ttgcagagca gcaccctgta acgtttgtca gaaatttccg    840
cgggctggct gaactttga aagtgagcgg gaaaatgcag aagcgtgatt ggaagactaa     900
tgtacacgtc attgtgggc cacctgggtg tggtaaaagc aaatgggctg ctaattttgc    960
agacccggaa accacatact ggaaaccacc tagaaacaag tggtgggatg gttaccatgg   1020
tgaagaagtg gttgttattg atgactttta tggctggctg ccctgggatg atctactgag   1080
actgtgtgat cgatatccat tgactgtaga gactaaaggt ggaactgtac cttttttggc   1140
ccgcagtatt ctgattacca gcaatcagac cccgttggaa tggtactcct caactgctgt   1200
cccagctgta gaagctcttt atcggaggat tacttccttg gtattttgga gaatgctac    1260 agaacaatcc acggaggaag ggggccagtt cgtcacccct tcccccccat gccctgaatt   1320
tccatatgaa ataaattact gagtcttttt tatcacttcg taatggtttt tattattcat   1380
taagggttaa gtgggggggtc tttaagatta aattctctga attgtacata catgttaca   1440 cggatattgt attcctggtc gtatatactg ttttcgaacg cagtgccgag gcctacgtgg   1500
tctacatttc cagtagtttg tagtctcagc cacagctgat ttcttttgtt gtttggttgg   1560
aagtaatcaa tagtggaatc taggacaggt ttgggggtaa agtagcggga gtggtaggag   1620
aagggctggg ttatggtatg gcgggaggag tagtttacat aggggtcata ggtgagggct   1680
gtggcctttg ttacaaagtt atcatctaga ataacagcac tggagcccac tcccctgtca   1740
ccctgggtga tcggggagca gggccag                                      1767
```

<210> SEQ ID NO 3
<211> LENGTH: 1768
<212> TYPE: DNA
<213> ORGANISM: Porcine circovirus

<400> SEQUENCE: 3

```
aattcaacct taacctttt tattctgtag tattcaaagg gtatagagat tttgttggtc     60
ccccctcccg ggggaacaaa gtcgtcaata ttaaatctca tcatgtccac cgcccaggag    120
ggcgttctga ctgtggtagc cttgacagta tatccgaagg tgcgggagag gcgggtgttg   180
aagatgccat ttttccttct ccaacggtag cggtggcggg ggtggacgag ccaggggcgg    240
cggcggagga tctggccaag atggctgcgg gggcggtgtc ttcttctgcg gtaacgcctc   300
cttggatacg tcatagctga aaacgaaaga agtgcgctgt aagtattacc agcgcacttc    360
ggcagcggca gcacctcggc agcacctcag cagcaacatg cccagcaaga agaatggaag   420
aagcggaccc caaccacata aaaggtgggt gttcacgctg aataatcctt ccgaagacga    480
gcgcaagaaa atacgggagc tcccaatctc cctatttgat tattttattg ttggcgagga   540
gggtaatgag gaaggacgaa cacctcacct ccagggggttc gctaattttg tgaagaagca   600
aacttttaat aaagtgaagt ggtatttggg tgcccgctgc cacatcgaga aagcaaaagg    660
aactgatcag cagaataaag aatattgcag taaagaaggc aacttactta ttgaatgtgg   720
```

-continued

| | |
|---|---|
| agctcctcga tctcaaggac aacggagtga cctgtctact gctgtgagta ccttgttgga | 780 |
| gagcgggagt ctggtgaccg ttgcagagca gcaccctgta acgtttgtca gaaatttccg | 840 |
| cgggctggct gaacttttga aagtgagcgg gaaaatgcag aagcgtgatt ggaagaccaa | 900 |
| tgtacacgtc attgtgggc cacctggtg tggtaaaagc aaatgggctg ctaattttgc | 960 |
| agacccggaa accacatact ggaaaccacc tagaaacaag tggtgggatg gttaccatgg | 1020 |
| tgaagaagtg gttgttattg atgactttta tggctggctg ccgtgggatg atctactgag | 1080 |
| actgtgtgat cgatatccat tgactgtaga gactaaaggt ggaactgtac cttttttggc | 1140 |
| ccgcagtatt ctgattacca gcaatcagac cccgttggaa tggtactcct caactgctgt | 1200 |
| cccagctgta gaagctctct atcggaggat tacttccttg gtattttgga gaatgctac | 1260 |
| agaacaatcc acggaggaag ggggccagtt cgtcacccct tcccccccat gccctgaatt | 1320 |
| tccatatgaa ataaattact gagtcttttt tatcacttcg taatggtttt tattattcat | 1380 |
| ttagggttta agtgggggt ctttaagatt aaattctctg aattgtacat acatggttac | 1440 |
| acggatattg tagtcctggt cgtatatact gttttcgaac gcagtgccga ggcctacgtg | 1500 |
| gtccacattt ctagaggttt gtagcctcag ccaaagctga ttccttttgt tatttggttg | 1560 |
| gaagtaatca atagtggagt caagaacagg tttgggtgtg aagtaacggg agtggtagga | 1620 |
| gaagggttgg gggattgtat ggcgggagga gtagtttaca tatgggtcat aggttagggc | 1680 |
| tgtggccttt gttacaaagt tatcatctag aataacagca gtggagccca ctcccctatc | 1740 |
| accctgggtg atgggggagc agggccag | 1768 |

<210> SEQ ID NO 4
<211> LENGTH: 1768
<212> TYPE: DNA
<213> ORGANISM: Porcine circovirus

<400> SEQUENCE: 4

| | |
|---|---|
| aattcaacct taacctttct tattctgtag tattcaaagg gtatagagat tttgttggtc | 60 |
| cccctcccg gggaacaaa gtcgtcaatt ttaaatctca tcatgtccac cgcccaggag | 120 |
| ggcgttgtga ctgtggtacg cttgacagta tatccgaagg tgcgggagag gcgggtgttg | 180 |
| aagatgccat ttttccttct ccaacggtag cgtggcggg ggtggacgag ccaggggcgg | 240 |
| cggcggagga tctggccaag atggctgcgg gggcggtgtc ttcttctgcg gtaacgcctc | 300 |
| cttggatacg tcatagctga aaacgaaaga agtgcgctgt aagtattacc agcgcacttc | 360 |
| ggcagcggca gcacctcggc agcacctcag cagcaacatg cccagcaaga gaatggaag | 420 |
| aagcggaccc caaccacata aaggtgggt gttcacgctg ataatccttc cgaagacga | 480 |
| gcgcaagaaa atacgggagc tcccaatctc cctatttgat tattttattg ttggcgagga | 540 |
| gggtaatgag gaaggacgaa cacctcacct ccagggttc gctaattttg tgaagaagca | 600 |
| aacttttaat aaagtgaagt ggtatttggg tgcccgctgc acatcgaga agccaaagg | 660 |
| aactgatcag cagaataaag aatattgcag taaagaaggc aacttactta ttgaatgtgg | 720 |
| agctcctcga tctcaaggac aacggagtga cctgtctact gctgtgagta ccttgttgga | 780 |
| gagcgggagt ctggtgaccg ttgcagagca gcaccctgta acgtttgtca gaaatttccg | 840 |
| cgggctggct gaacttttga aagtgagcgg gaaaatgcag aagcgtgatt ggaagaccaa | 900 |
| tgtacacgtc attgtgggc cacctggtg tggtaaaagc aaatgggctg ctaattttgc | 960 |
| agacccggaa accacatact ggaaaccacc tagaaacaag tggtgggatg gttaccatgg | 1020 |
| tgaagaagtg gttgttattg atgactttta tggctggctg ccgtgggatg atctactgag | 1080 |

-continued

```
actgtgtgat cgatatccat tgactgtaga gactaaaggt ggaactgtac cttttttggc      1140
ccgcagtatt ctgattacca gcaatcagac cccgttggaa tggtactcct caactgctgt      1200
cccagctgta gaagctctct atcggaggat tacttccttg gtattttgga agaatgctac      1260
agaacaatcc acggaggaag ggggccagtt cgtcacccct tcccccccat gccctgaatt      1320
tccatatgaa ataaattact gagtcttttt tatcacttcg taatggtttt tattattcat      1380
ttagggttta agtgggggg t ctttaagatt aaattctctg aattgtacat acatggttac      1440
acggatattg tagtcctggt cgtatttact gttttcgaac gcagcgccga ggcctacgtg      1500
gtccacattt ccagaggttt gtagtctcag ccaaagctga ttccttttgt tatttggttg      1560
gaagtaatca atagtggagt caagaacagg tttgggtgtg aagtaacggg agtggtagga      1620
gaagggttgg gggattgtat ggcgggagga gtagtttaca tatgggtcat aggttagggc      1680
tgtggccttt gttacaaagt tatcatctag aataacagca gtggagccca ctcccctatc      1740
accctgggtg atgggggagc agggccag                                        1768

<210> SEQ ID NO 5
<211> LENGTH: 1759
<212> TYPE: DNA
<213> ORGANISM: Porcine circovirus

<400> SEQUENCE: 5
aattcatatt tagcctttct aatacggtag tattggaaag gtaggggtag ggggttggtg        60
ccgcctgagg gggggaggaa ctggccgatg ttgaatttga ggtagttaac attccaagat       120
ggctgcgagt atcctccttt tatggtgagt acaaattctg tagaaaggcg ggaattgaag       180
atacccgtct ttcggcgcca tctgtaacgg tttctgaagg cggggtgtgc caaatatggt       240
cttctccgga ggatgtttcc aagatggctg cgggggcggg tccttcttct gcggtaacgc       300
ctccttggcc acgtcatcct ataaaagtga agaagtgcg ctgctgtagt attaccagcg       360
cacttcggca gcggcagcac ctcggcagcg tcagtgaaaa tgccaagcaa gaaaagcggc       420
ccgcaacccc ataagaggtg ggtgttcacc cttaataatc cttccgagga ggagaaaaac       480
aaaatacggg agcttccaat ctccctttt gattattttg tttgcggaga ggaaggtttg       540
gaagagggta gaactcctca cctccagggg tttgcgaatt tgctaagaa gcagactttt       600 aacaaggtga agtggtattt tggtgcccgc tgccacatcg agaaagcgaa aggaaccgac       660
cagcagaata agaatactg cagtaaagaa ggccacatac ttatcgagtg tggagctccg       720
cggaaccagg ggaagcgcag cgacctgtct actgctgtga gtacccttt ggagacgggg       780 tctttggtga ctgtagccga gcagttccct gtaacgtatg tgagaaattt ccgcgggctg       840
gctgaacttt tgaaagtgag cgggaagatg cagcagcgtg attggaagac agctgtacac       900
gtcatagtgg gcccgcccgg ttgtgggaag agccagtggg cccgtaattt tgctgagcct       960
agggacacct actggaagcc tagtagaaat aagtggtggg atggatatca tggagaagaa      1020
gttgttgttt tggatgattt ttatggctgg ttaccttggg atgatctact gagactgtgt      1080
gaccggtatc cattgactgt agagactaaa ggggtactg ttccttttttt ggcccgcagt      1140 attttgatta ccagcaatca ggcccccag gaatggtact cctcaactgc tgtcccagct      1200
gtagaagctc tctatcggag gattactact ttgcaatttt ggaagactgc tggagaacaa      1260
tccacggagg tacccgaagg ccgatttgaa gcagtggacc caccctgtgc cctttttccca      1320 tataaaataa attactgagt cttttttgtt atcacatcgt aatggttttt atttttattt      1380
```

-continued

```
atttagaggg tctttagga taaattctct gaattgtaca taaatagtca gccttaccac    1440
ataattttgg gctgtggctg cattttggag cgcatagccg aggcctgtgt gctcgacatt    1500
ggtgtgggta tttaaatgga gccacagctg gtttctttta ttatttgggt ggaaccaatc    1560
aattgtttgg tccagctcag gtttgggggt gaagtacctg gagtggtagg taaagggctg    1620
ccttatggtg tggcgggagg agtagttaat atagggtca taggccaagt tggtggaggg    1680
ggttacaaag ttggcatcca agataacaac agtggaccca acacctcttt gattagaggt    1740 gatgggtct ctggggtaa                                                  1759
```

<210> SEQ ID NO 6
<211> LENGTH: 1768
<212> TYPE: DNA
<213> ORGANISM: Porcine circovirus
<220> FEATURE:
<221> NAME/KEY: variation
<222> LOCATION: (1)..(1768)
<223> OTHER INFORMATION: N represents A or C or G or T

<400> SEQUENCE: 6

```
gaattcaacc ttaaccttt ttattctgta gtattcaaag ggtataaaga ttttgttggt      60
cccccctccc gggggaacaa agtcgtcaat attaaatctc atcatgtcca ccgcccagga    120
gggcgttctg actgtggtag ccttgacagt atatccgaag gtgcgggaga rgcgggtgtt    180
gaaaatgcca ttttccttc tccaacggta gcggtggcgg gggtggacma nccacgggcg    240
gcggcggawg atctggccaa gatggctgcg ggggcggtgt cttcttctgc ggtaacgcct    300
ccttggatac gtcatagctg aaaacgaaag aagtgcgctg taagtattac cagcgcactt    360
cggcagcggc agcacctcgg cagcacctca gcagcaacat gcccagcaag aagaatggaa    420
gaagcggacc ccaaccacat aaaaggtggg tgttcacgct gaataatcct tccgaagacg    480
agcgcaagaa aatacgggag ctcccaatct ccctatttga ttatttatt gttggcgagg    540 agggtwwtga ggaangacga acacctcacc tccaggggtt cgctaatttt gtgaagaagc    600 aaactttaa taaagtgaag tggtatttgg gtgcccgctg ccacatcgag aaagccaaag    660
gaactgatca gcagaataaa gaatattgca gtaaagaagg caacttactt attgaatgtg    720
gagctcctcg atctcaagga caacggagtg acctgtctac tgctgtgagt accttgttgg    780
agagcgggag tctggtgacc gttgcagagc agcaccctgt aacgtttgtc agaaatttcc    840
gcgggctggc tgaactttg aaagtgagcg ggaaaatgca gaagcgtgat tggaagacca    900
atgtacacgt cattgtgggg ccacctgggt gtggtaaaag caaatgggct gctaattttg    960
cagacccgga aaccacatac tggaaaccac ctagaaacaa gtggtgggat ggttaccatg   1020
gtgaagaagt ggttgttatt gatgactttt atggctggct gccgtgggat gatctactga   1080
gactgtgtga tcgatatcca ttgactgtag agactaaagg tggaactgta cnnnnnnngg   1140
cccgcagtat tctgattacc agcaatcaga ccccgttgga atggtactcc tcaactgctg   1200
tcccagctgt agaagctctc tatcggagga ttacttcctt ggtattttgg aagaatgcta   1260
cagaacaatc cacggaggaa gggggccagt tngtcaccct ttcccccca tgccctgaat   1320 ttccatatga aataaattac tgagtctttt ttatcacttc gtaatggttt ttattattca   1380
tttagggttt aagtggggg tctttaagat taaattctct gaattgtaca tacatggtta   1440
cacggatatt gtagtcctgg tcgtatatac tgttttcgaa cgcagtgccg aggcctacgt   1500
ggtccacatt tctagaggtt tgtagcctca gccaaagctg attccttttg ttatttggtt   1560
ggaagtaatc aatagtggag tcaagaacag gtttgggtgt gaagtaacgg gagtggtagg   1620
```

-continued

```
agaagggttg ggggattgta tggcgggagg agtagtttac atatgggtca taggttaggg   1680
ctgtggcctt tgttacaaag ttatcatcta gaataacagc agtggagccc actcccctat   1740
caccctgggt gatgggggag cagggcca                                     1768
```